United States Patent [19]
McDevitt et al.

[11] Patent Number: 6,146,846
[45] Date of Patent: Nov. 14, 2000

[54] **PRIMOSOME PROTEIN A OF *STREPTOCOCCUS PNEUMONIAE***

[75] Inventors: Damien McDevitt, Berwyn; Lisa K Shilling, Newton; Annemarie St. John, Pottstown; Richard L Warren, Blue Bell, all of Pa.

[73] Assignee: SmithKline Beecham Corporation, Philadelphia, Pa.

[21] Appl. No.: 09/067,091

[22] Filed: Apr. 27, 1998

[51] Int. Cl.$^7$ .......................... C12N 15/31; C12N 15/52; C12N 15/62; C12N 15/63; C07H 21/00

[52] U.S. Cl. ................. 435/69.1; 435/252.3; 435/254.11; 435/320.1; 435/325; 435/455; 435/471; 536/23.1; 536/23.2; 536/23.4; 536/23.7

[58] Field of Search .................................. 536/23.1, 23.2, 536/23.7, 23.4; 435/69.1, 320.1, 325, 252.3, 254.11, 455, 471; 514/44

[56] References Cited

FOREIGN PATENT DOCUMENTS

WO 97/43303   11/1997   WIPO.

OTHER PUBLICATIONS

Ngo et al., "Computational complexity, protein structure prediction, and the Levinthal paradox", in The Protein Folding Problem and Tertiary Structure Prediction, Merz et al. (eds.), Birkhauser Boston: Boston, MA, pp. 433 and 492–495, 1994.

Rudinger, "Characteristics of the amino acids as componants of a peptide hormone sequence", in Peptide Hormones, Parsons (ed.), University Park Press: Baltimore, MD, pp. 1–7, Jun. 1976.

Swissprot Submission, Accession No. P94461, Direct Submission, Nov. 1,1997.

GenBank Submission, Accession No. Y13937, Direct Submission, Mar. 30, 1998.

Eui Hum Lee, et al, "The priA Gene Encoding the Primosomal Replicative n' Protein of *Escherichia coli*", Proc. Natl. Acad. Sci. USA, vol. 87, pp. 4620–4624, Jun. 1990.

*Primary Examiner*—Scott D. Priebe
*Attorney, Agent, or Firm*—Edward R. Gimmi; Thomas S. Deibert; William T. King

[57]  ABSTRACT

The invention provides priA polypeptides and polynucleotides encoding priA polypeptides and methods for producing such polypeptides by recombinant techniques. Also provided are methods for utilizing priA polypeptides to screen for antibacterial compounds.

26 Claims, No Drawings

PRIMOSOME PROTEIN A OF STREPTOCOCCUS PNEUMONIAE

FIELD OF THE INVENTION

This invention relates to newly identified polynucleotides and polypeptides, and their production and uses, as well as their variants, agonists and antagonists, and their uses. In particular, the invention relates to polynucleotides and polypeptides of the primosome family, as well as their variants, hereinafter referred to as "priA," "priA polynucleotide(s)," and "priA polypeptide(s)."

BACKGROUND OF THE INVENTION

The Streptococci make up a medically important genera of microbes known to cause several types of disease in humans, including, for example, otitis media, conjunctivitis, pneumonia, bacteremia, menigitis, sinusitis, pleural empyema and endocarditis, and most particularly meningitis, such as for example infection of cerebrospinal fluid. Since its isolation more than 100 years ago, *Streptococcus pneumoniae* has been one of the more intensively studied microbes. For example, much of our early understanding that DNA is, in fact, the genetic material was predicated on the work of Griffith and of Avery, Macleod and McCarty using this microbe. Despite the vast amount of research with *S. pneumoniae*, many questions concerning the virulence of this microbe remain. It is particularly preferred to employ Streptococcal genes and gene products as targets for the development of antibiotics.

The frequency of *Streptococcus pneumoniae* infections has risen dramatically in the past few decades. This has been attributed to the emergence of multiply antibiotic resistant strains and an increasing population of people with weakened immune systems. It is no longer uncommon to isolate *Streptococcus pneumoniae* strains which are resistant to some or all of the standard antibiotics. This phenomenon has created an unmet medical need and demand for new antimicrobial agents, vaccines, drug screening methods, and diagnostic tests for this organism.

Moreover, the drug discovery process is currently undergoing a fundamental revolution as it embraces "functional genomics," that is, high throughput genome- or gene-based biology. This approach is rapidly superseding earlier approaches based on "positional cloning" and other methods. Functional genomics relies heavily on the various tools of bioinformatics to identify gene sequences of potential interest from the many molecular biology databases now available as well as from other sources. There is a continuing and significant need to identify and characterize further genes and other polynucleotides sequences and their related polypeptides, as targets for drug discovery.

Clearly, there exists a need for polynucleotides and polypeptides, such as the priA embodiments of the invention, that have a present benefit of, among other things, being useful to screen compounds for antibiotic activity. Such factors are also useful to determine their role in pathogenesis of infection, dysfunction and disease. There is also a need for identification and characterization of such factors and their antagonists and agonists to find ways to prevent, ameliorate or correct such infection, dysfunction and disease.

Certain of the polypeptides of the invention possess significant amino acid sequence homology to known priA in *B. subtilis* (p94461), in *H. influenzae* (P44647), in *E. coli* (P17888), and in *R. rubrum* (P05445), and a low sequence homology to a protein in *S. cerevisiae* (p20449).

SUMMARY OF THE INVENTION

The present invention relates to priA, in particular priA polypeptides and priA polynucleotides, recombinant materials and methods for their production. In another aspect the invention relates to methods for using such polypeptides and polynucleotides, including the treatment of microbial diseases, amongst others. In a further aspect, the invention relates to methods for identifying agonists and antagonists using the materials provided by the invention, and for treating microbial infections and conditions associated with such infections with the identified compounds. In a still further aspect, the invention relates to diagnostic assays for detecting diseases associated with microbial infections and conditions associated with such infections, such as assays for detecting priA expression or activity.

Various changes and modifications within the spirit and scope of the disclosed invention will become readily apparent to those skilled in the art from reading the following descriptions and from reading the other parts of the present disclosure.

DESCRIPTION OF THE INVENTION

The invention relates to priA polypeptides and polynucleotides as described in greater detail below. In particular, the invention relates to polypeptides and polynucleotides of a priA of *Streptococcus pneumoniae*, which is related by amino acid sequence homology to priA in *B. subtilis* (p94461), in *H. influenzae* (P44647), in *E. coli* (P17888), and in *R. rubrum* (P05445), and related with a low sequence homology to a protein in *S. cerevisiae* (p20449) polypeptide. The invention relates especially to priA having the nucleotide and amino acid sequences set out in Table 1 as SEQ ID NO: 1 and SEQ ID NO: 2 respectively.

TABLE 1

PriA Polynucleotide and Polypeptide Sequences (A) *Streptococcus pneumoniae* priA polynucleotide sequence [SEQ ID NO: 1].

5'-TTCGATTTGCTGAAACGTGTCAAATGTGTGATTGAAGCAGAACACTTCTG

TGTGGATCGTGTCATTGGTCACTATCAGGAGATGTTACCAAAATCTCCAA

CTACCCGATAAAATTTAGAAAATAGGTACAAGCAAATGATGTTAAAACCC

TCTATTGATACCTTGCTCGACAAGGTTCCTTCAAAATATTCACTCGTAAT

TABLE 1-continued

PriA Polynucleotide and Polypeptide Sequences

CTTGGAAGCAAAACGTGCCCACGAATTGGAAGCAGGTGCCCCAGCAACTC

AAGGTTTCAAGTCTGAAAAATCAACTCTTCGCGCTTTAGAAGAAATCGAA

TCAGGAAACGTTACAATTCACCCAGATCCAGAAGGAAAACGTGAAGCAGT

GCGTCGCCGTATCGAAGAAGAAAAACGCCGCAAAGAAGAAGAAGAAAAGA

AAATCAAAGAGCAAATTGCTAAAGAAAAAGAAGATGGTGAAAAAATTTAA

GGTTGGGGGGACTCAATCTTATTTTTTCTATTGCAAGAATGTACTGACAA

GGAGGAGGTGAGAAGATGGCCCTAGCTAAGATTATCGTAGATGTGCCCTT

GATGCAGACGGACCAGCCCTATAGTTACAGGATTCCGGAGGAATTTGAGG

GAATGCTGGAAGTTGGGATGCGGGTTCATGTGCCTTTTGGTAAGGGTAAT

CGCCTGATTCAAGGGATTGTTCTTGGTTTGGAGTCCCAATCAGATGGAGA

AGAGATGGAGCAAGATTTAAAAGATATTGCAGAGGTGCTGGATTTTTCTC

CTGTTCTCACGCCAGAACAACTCTGGCTGGCTGAGGAGTTACGCAAATCT

GTCTTCTCCTACAAAATTTCTATCCTCAAGGCCATGCTTCCAGGATTTCT

GAATTCTAGCTATGACAAGATTCTCTATCCTCTGGAAGGCTTGAGTCAGG

AAGAACGAGTGCGCCTGTTTGGTTCAGAAGATTCGCTAGCCTTTTCTTCA

CTAGACCTTGCCAAGCAAGCTGAAATGATGCGTTTGACTAGAAAAGGCCT

GCTTGGTCTGGAATATCAGGCAGTCGATCAAAAGAAGGTCAAGACCCAGT

CTTGGTATGAGGTTGACCATGCTCAATTAGAAGGTGTTGAGATTTCTACA

CGTGCCAAGAAAAAGTTGGAACTGAGAGATTATCTGCTGTCTCATCCAGA

GAGCGCTTCCTTGGCTAGCTTGTTAGAGTCCTACTCGCGAGAGCAAGTCA

ACTTCTTTGTGGATCAAGGTGCTGTTACCATAGTCCAAAAGGAAGTTCAA

CGCTCGGCTGCTTATTTTGAAGGAATTGAAGCAAGTAGACCTTTGGAGTT

AAATCCAGAACAAAGACAGGCGCGTGATGCGGTTGTGAGTTCTATTGGCA

GTTCTCAACCTCCCTTTCTACTTCAAGGGATTACAGGAAGTGGGAAGACC

GAGGTTTACTTGCAGATTATCCAAGGTGCCCTGGATAAGGGCAAGACAGC

TATTTTGCTGGTACCTGAGATTTCCTTGACTCCTCAGATGACCGAGCGTT

TTATAGCACGTTTTGGGGACAAGGTAGCCATTCTTCACTCAGGATTATCC

AATGGTGAAAAGTATGATGAATGCGCAAGGTGGAGCGTGGCGATGCCCA

AGTTGTTGTTGGTGCCAGATCTGCTATCTTTGCTCCTCTGAAAAATCTGG

GTGTCATGATTATTGATGAAGAGCATGAAGCGGCTTATAAGCAGGACAGC

AATCCCCGTTACCATGCCAGAGAGGTAGCTATTTTACGGGCTCAGTATAA

TCAAGCAACTCTGGTACTTGGATCTGCAACGCCGAGCTTAGAGAGCCGGG

CACGTGCTGGCAAAGGCGTCTATCAACACTTACGTCTAACCCAACGTGCC

AATCCTTTGGCTACAATCCCTGAGGTTCAAGTGATTGACTTTCGAGACTA

TATCGGACAAAATGAGACGTCAAACTTTACGCCTCCTTTGCTAGAGGCTA

TCCAAGACCGTCTGGTTAAAAAAGAGCAGATGGTTCTCATGCTCAATCGC

CGTGGTTATTCTAGCTTTGTCATGTGTCGGGAGTGTGGGACGGTGGATAC

TTGTCCCAACTGTGATATTTCTCTGACCTTGCATATGGATACCAAGACTA

TGAACTGCCATTATTGTGGTTTCTCGAAGGATATTCCTCAGGTCTGTCCT

TABLE 1-continued

PriA Polynucleotide and Polypeptide Sequences

AACTGTAAGAGCCACAGTATTCGTTACTATGGGACGGGAACTCAGAAGGC

TTATGATGAGCTAGCAGAACTCTTTCCCCAAGCTCGCATTTTGAGGATGG

ATGTGGATACGACTCGAAAGAAAGGCAGTCACCAAGCCTTGCTTGACCAG

TTTGGGCGAGGGGAAGCGGATATTTTACTTGGTACTCAGATGATTGCAAA

GGGTTTGGATTTTCCCAATGTTACCCTAGTCGGAGTTCTAAATGCGGATA

CGGCCTTGAATCTGCCTGATTTCCGTTCTTCTGAGAGAACCTTCCAGCTC

TTGACTCAGGTGGCAGGTCGAGCAGGTCGTGCTGAAAAGGCAGGTCAAGT

CTTGATACAGTCCTACAATCCGCAGCACTATGCTATTCGATTTGCCAAGG

ATCAAGATTACGAAGGCTTTTATGCCTATGAAATGGGAATCAGACGACAA

CTCGGCTATCCACCTTACTATTTCACGATTGGTATTACCCTTTCTCACAA

GAAAGAAGAAGAGGTTTTCAAACGTGCCTATGAAGTCATGAACATTTTGC

GGTCAGGCTTGTCAGAGACCAGTCCCATTCTGGGGCCAACGCCAAAACCG

ATTGCCCGTACCCACAACCTCTATCATTACCAGATTTTAATTAAATACCG

TTTAGAAGATGAGCTGGGGCCGACCCTCAACCAGGTCCTGGCCTTGACTC

AAGAACGGGAAAATAGTGAGCTCCGTCTCAGCATTGACCATGAGCCGCAG

CAATTTTTATAAGAAGGAGAAGATATGACAAAACTAATCTTTATGGGGAC

CCCCGACTTTTCAGCAACAGTCTTAAAAGGACTTTTGACAGATGACCGTT

ACGAAATTCTAGCCG-3'

(D) *Streptococcus pneumoniae* priA polypeptide sequence deduced
from a polynucleotide sequence in this table [SEQ ID NO:2].

NH$_2$-QGGGEKMALAKIIVDVPLMQTDQPYSYRIPEEFEGMLEVGMRVHVPFGKGNRLIQGIVLG

LESQSDGEEMEQDLKDIAEVLDFSPVLTPEQLWLAEELRKSVFSYKISILKAMLPGFLNS

SYDKILYPLEGLSQEERVRLFGSEDSLAFSSLDLAKQAEMMRLTRKGLLGLEYQAVDQKK

VKTQSWYEVDHAQLEGVEISTRAKKKLELRDYLLSHPESASLASLLESYSREQVNFFVDQ

GAVTIVQKEVQRSAAYFEGIEASRPLELNPEQRQARDAVVSSIGSSQPPFLLQGITGSGK

TEVYLQIIQGALDKGKTAILLVPEISLTPQMTERFIARFGDKVAILHSGLSNGEKYDEWR

KVERGDAQVVVGARSAIFAPLKNLGVMIIDEEHEAAYKQDSNPRYHAREVAILRAQYNQA

TLVLGSATPSLESRARAGKGVYQHLRLTQRANPLATIPEVQVIDFRDYIGQNETSNFTPP

LLEAIQDRLVKKEQMVLMLNRRGYSSFVMCRECGTVDTCPNCDISLTLHMDTKTMNCHYC

GFSKDIPQVCPNCKSHSIRYYGTGTQKAYDELAELFPQARILRMDVDTTRKKGSHQALLD

QFGRGEADILLGTQMIAKGLDFPNVTLVGVLNADTALNLPDFRSSERTFQLLTQVAGRAG

RAEKAGQVLIQSYNPQHYAIRFAKDQDYEGFYAYEMGIRRQLGYPPYYFTIGITLSHKKE

EEVFKRAYEVMNILRSGLSETSPILGPTPKPIARTHNLYHYQILIKYRLEDELGPTLNQV

LALTQERENSELRLSIDHEPQQFL-COOH (C) *Streptococcus pneumoniae* priA polynucleotide sequence
[SEQ ID NO:5] (open reading frame and stop codon).

| | |
|---|---|
| CAA GGAGGAGGTG AGAAGATGGC CCTAGCTAAG ATTATCGTAG | 540 |
| ATGTGCCCTT GATGCAGACG GACCAGCCCT ATAGTTACAG GATTCCGGAG GAATTTGAGG | 600 |
| GAATGCTGGA AGTTGGGATG CGGGTTCATG TGCCTTTTGG TAAGGGTAAT CGCCTGATTC | 660 |

TABLE 1-continued

PriA Polynucleotide and Polypeptide Sequences

```
AAGGGATTGT TCTTGGTTTG GAGTCCCAAT CAGATGGAGA AGAGATGGAG CAAGATTTAA    720

AAGATATTGC AGAGGTGCTG GATTTTTCTC CTGTTCTCAC GCCAGAACAA CTCTGGCTGG    780

CTGAGGAGTT ACGCAAATCT GTCTTCTCCT ACAAAATTTC TATCCTCAAG GCCATGCTTC    640

CAGGATTTCT GAATTCTAGC TATGACAAGA TTCTCTATCC TCTGGAAGGC TTGAGTCAGG    900

AAGAACGAGT GCGCCTGTTT GGTTCAGAAG ATTCGCTAGC CTTTTCTTCA CTAGACCTTG    960

CCAAGCAAGC TGAAATGATG CGTTTGACTA GAAAAGGCCT GCTTGGTCTG GAATATCAGG   1020

CAGTCGATCA AAAGAAGGTC AAGACCCAGT CTTGGTATGA GGTTGACCAT GCTCAATTAG   1080

AAGGTGTTGA GATTTCTACA CGTGCCAAGA AAAAGTTGGA ACTGAGAGAT TATCTGCTGT   1140

CTCATCCAGA GAGCGCTTCC TTGGCTAGCT TGTTAGAGTC CTACTCGCGA GAGCAAGTCA   1200

ACTTCTTTGT GGATCAAGGT GCTGTTACCA TAGTCCAAAA GGAAGTTCAA CGCTCGGCTG   1260

CTTATTTTGA AGGAATTGAA GCAAGTAGAC CTTTGGAGTT AAATCCAGAA CAAAGACAGG   1320

CGCGTGATGC GGTTGTGAGT TCTATTGGCA GTTCTCAACC TCCCTTTCTA CTTCAAGGGA   1380

TTACAGGAAG TGGGAAGACC GAGGTTTACT TGCAGATTAT CCAAGGTGCC CTGGATAAGG   1440

GCAAGACAGC TATTTTGCTG GTACCTGAGA TTTCCTTGAC TCCTCAGATG ACCGAGCGTT   1500

TTATAGCACG TTTTGGGGAC AAGGTAGCCA TTCTTCACTC AGGATTATCC AATGGTGAAA   1560

AGTATGATGA ATGGCGCAAG GTGGAGCGTG GCGATGCCCA AGTTGTTGTT GGTGCCAGAT   1620

CTGCTATCTT TGCTCCTCTG AAAAATCTGG GTGTCATGAT TATTGATGAA GAGCATGAAG   1680

CGGCTTATAA GCAGGACAGC AATCCCCGTT ACCATGCCAG AGAGGTAGCT ATTTTACGGG   1740

CTCAGTATAA TCAAGCAACT CTGGTACTTG GATCTGCAAC GCCGAGCTTA GAGAGCCGGG   1800

CACGTGCTGG CAAAGGCGTC TATCAACACT TACGTCTAAC CCAACGTGCC AATCCTTTGG   1860

CTACAATCCC TGAGGTTCAA GTGATTGACT TTCGAGACTA TATCGGACAA AATGAGACGT   1920

CAAACTTTAC GCCTCCTTTG CTAGAGGCTA TCCAAGACCG TCTGGTTAAA AAAGAGCAGA   1980

TGGTTCTCAT GCTCAATCGC CGTGGTTATT CTAGCTTTGT CATGTGTCGG GAGTGTGGGA   2040

CGGTGGATAC TTGTCCCAAC TGTGATATTT CTCTGACCTT GCATATGGAT ACCAAGACTA   2100

TGAACTGCCA TTATTGTGGT TTCTCGAAGG ATATTCCTCA GGTCTGTCCT AACTGTAAGA   2160

GCCACAGTAT TCGTTACTAT GGGACGGGAA CTCAGAAGGC TTATGATGAG CTAGCAGAAC   2220

TCTTTCCCCA AGCTCGCATT TTGAGGATGG ATGTGGATAC GACTCGAAAG AAAGGCAGTC   2280

ACCAAGCCTT GCTTGACCAG TTTGGGCGAG GGGAAGCGGA TATTTTACTT GGTACTCAGA   2340

TGATTGCAAA GGGTTTGGAT TTTCCCAATG TTACCCTAGT CGGAGTTCTA AATGCGGATA   2400

CGGCCTTGAA TCTGCCTGAT TTCCGTTCTT CTGAGAGAAC CTTCCAGCTC TTGACTCAGG   2460

TGGCAGGTCG AGCAGGTCGT GCTGAAAAGG CAGGTCAAGT CTTGATACAG TCCTACAATC   2520

CGCAGCACTA TGCTATTCGA TTTGCCAAGG ATCAAGATTA CGAAGGCTTT TATGCCTATG   2580

AAATGGGAAT CAGACGACAA CTCGGCTATC CACCTTACTA TTTCACGATT GGTATTACCC   2640

TTTCTCACAA GAAAGAAGAA GAGGTTTTCA AACGTGCCTA TGAAGTCATG AACATTTTGC   2700

GGTCAGGCTT GTCAGAGACC AGTCCCATTC TGGGGCCAAC GCCAAAACCG ATTGCCCGTA   2760

CCCACAACCT CTATCATTAC CAGATTTTAA TTAAATACCG TTTAGAAGAT GAGCTGGGGC   2820

CGACCCTCAA CCAGGTCCTG GCCTTGACTC AAGAACGGGA AAATAGTGAG CTCCGTCTCA   2880

GCATTGACCA TGAGCCGCAG CAATTTTTAT AA
```

Deposited Materials

A deposit containing a *Streptococcus pneumoniae* 0100993 strain has been deposited with the National Collections of Industrial and Manne Bacteria Ltd. (herein "NCIMB"), 23 St. Machar Drive, Aberdeen AB2 1RY, Scotland on Apr. 11, 1996 and assigned deposit number 40794. The deposit was described as *Streptococcus pneumoniae* 0100993 on deposit. On Apr. 17, 1996 a *Streptococcus pneumoniae* 0100993 DNA library in *E. coli* was similarly deposited with the NCIMB and assigned deposit number 40800. The *Streptococcus pneumoniae* strain deposit is referred to herein as "the deposited strain" or as "The DNA of the deposited strain."

The deposited strain contains the full length priA gene. The sequence of the polynucleotides contained in the deposited strain, as well as the amino acid sequence of any polypeptide encoded thereby, are controlling in the event of any conflict with any description of sequences herein.

The deposit of the deposited strain has been made under the terms of the Budapest Treaty on the International Recognition of the Deposit of Micro-organisms for Purposes of Patent Procedure. The strain will be irrevocably and without restriction or condition released to the public upon the issuance of a patent. The deposited strain is provided merely as convenience to those of skill in the art and is not an admission that a deposit is required for enablement, such as that required under 35 U.S.C. §112.

A license may be required to make, use or sell the deposited strain, and compounds derived therefrom, and no such license is hereby granted.

In one aspect of the invention there is provided an isolated nucleic acid molecule encoding a mature polypeptide expressible by the *Streptococcus pneumoniae* 0100993 strain, which polypeptide is contained in the deposited strain. Further provided by the invention are priA polynucleotide sequences in the deposited strain, such as DNA and RNA, and amino acid sequences encoded thereby. Also provided by the invention are priA polypeptide and polynucleotide sequences isolated from the deposited strain.

Polypeptides

PriA polypeptide of the invention is substantially phylogenetically related to other proteins of the primosome family.

In one aspect of the invention there are provided polypeptides of *Streptococcus pneumoniae* referred to herein as "priA" and "priA polypeptides" as well as biologically, diagnostically, prophylactically, clinically or therapeutically useful variants thereof, and compositions comprising the same.

Among the particularly preferred embodiments of the invention are variants of priA polypeptide encoded by naturally occurring alleles of the priA gene.

The present invention further provides for an isolated polypeptide which:

(a) comprises or consists of an amino acid sequence which has at least 70% identity, preferably at least 80% identity, more preferably at least 90% identity, yet more preferably at least 95% identity, most preferably at least 97–99% or exact identity, to that of SEQ ID NO:2 over the entire length of SEQ ID NO:2;

(b) a polypeptide encoded by an isolated polynucleotide comprising or consisting of a polynucleotide sequence which has at least 70% identity, preferably at least 80% identity, more preferably at least 90% identity, yet more preferably at least 95% identity, even more preferably at least 97–99% or exact identity to SEQ ID NOs:1 or 5 over the entire length of SEQ ID NOs:1 or 5;

(c) a polypeptide encoded by an isolated polynucleotide comprising or consisting of a polynucleotide sequence encoding a polypeptide which has at least 70% identity, preferably at least 80% identity, more preferably at least 90% identity, yet more preferably at least 95% identity, even more preferably at least 97–99% or exact identity, to the amino acid sequence of SEQ ID NO:2, over the entire length of SEQ ID NO:2.

The polypeptides of the invention include a polypeptide of Table 1 [SEQ ID NO:2] (in particular the mature polypeptide) as well as polypeptides and fragments, particularly those which have the biological activity of priA, and also those which have at least 70% identity to a polypeptide of Table 1 [SEQ ID NO:2] or the relevant portion, preferably at least 80% identity to a polypeptide of Table 1 [SEQ ID NO:2] and more preferably at least 90% identity to a polypeptide of Table 1 [SEQ ID NO:2] and still more preferably at least 95% identity to a polypeptide of Table 1 [SEQ ID NO:2] and also include portions of such polypeptides with such portion of the polypeptide generally containing at least 30 amino acids and more preferably at least 50 amino acids.

The invention also includes a polypeptide consisting of or comprising a polypeptide of the formula:

$$X\text{-}(R_1)_m\text{-}(R_2)\text{-}(R_3)_n\text{-}Y$$

wherein, at the amino terminus, X is hydrogen, a metal or any other moiety described herein for modified polypeptides, and at the carboxyl terminus, Y is hydrogen, a metal or any other moiety described herein for modified polypeptides, $R_1$ and $R_3$ are any amino acid residue or modified amino acid residue, m is an integer between 1 and 1000 or zero, n is an integer between 1 and 1000 or zero, and $R_2$ is an amino acid sequence of the invention, particularly an amino acid sequence selected from Table 1 or modified forms thereof In the formula above, $R_2$ is oriented so that its amino terminal amino acid residue is at the left, covalently bound to $R_1$, and its carboxy terminal amino acid residue is at the right, covalently bound to $R_3$. Any stretch of amino acid residues denoted by either $R_1$ or $R_3$, where m and/or n is greater than 1, may be either a heteropolymer or a homopolymer, preferably a heteropolymer. Other preferred embodiments of the invention are provided where m is an integer between 1 and 50, 100 or 500, and n is an integer between 1 and 50, 100, or 500.

It is most preferred that a polypeptide of the invention is derived from *Streptococcus pneumoniae*, however, it may preferably be obtained from other organisms of the same taxonomic genus. A polypeptide of the invention may also be obtained, for example, from organisms of the same taxonomic family or order.

A fragment is a variant polypeptide having an amino acid sequence that is entirely the same as part but not all of any amino acid sequence of any polypeptide of the invention. As with priA polypeptides, fragments may be "free-standing," or comprised within a larger polypeptide of which they form a part or region, most preferably as a single continuous region in a single larger polypeptide.

Preferred fragments include, for example, truncation polypeptides having a portion of an amino acid sequence of Table 1 [SEQ ID NO:2], or of variants thereof, such as a continuous series of residues that includes an amino- and/or carboxyl-terminal amino acid sequence. Degradation forms of the polypeptides of the invention produced by or in a host cell, particularly a *Streptococcus pneumoniae*, are also preferred. Further preferred are fragments characterized by structural or functional attributes such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions.

Further preferred fragments include an isolated polypeptide comprising an amino acid sequence having at least 15, 20, 30, 40, 50 or 100 contiguous amino acids from the amino acid sequence of SEQ ID NO: 2, or an isolated polypeptide comprising an amino acid sequence having at least 15, 20, 30, 40, 50 or 100 contiguous amino acids truncated or deleted from the amino acid sequence of SEQ ID NO: 2.

Also preferred are biologically active fragments which are those fragments that mediate activities of priA, including those with a similar activity or an improved activity, or with a decreased undesirable activity. Also included are those fragments that are antigenic or immunogenic in an animal, especially in a human. Particularly preferred are fragments comprising receptors or domains of enzymes that confer a function essential for viability of *Streptococcus pneumoniae* or the ability to initiate, or maintain cause Disease in an individual, particularly a human.

Fragments of the polypeptides of the invention may be employed for producing the corresponding full-length polypeptide by peptide synthesis; therefore, these variants may be employed as intermediates for producing the full-length polypeptides of the invention.

In addition to the standard single and triple letter representations for amino acids, the term "X" or "Xaa" may also be used in describing certain polypeptides of the invention. "X" and "Xaa" mean that any of the twenty naturally occurring amino acids may appear at such a designated position in the polypeptide sequence.

Polynucleotides

It is an object of the invention to provide polynucleotides that encode priA polypeptides, particularly polynucleotides that encode the polypeptide herein designated priA.

In a particularly preferred embodiment of the invention the polynucleotide comprises a region encoding priA polypeptides comprising a sequence set out in Table 1 [SEQ ID NOs:1 or 5] which includes a full length gene, or a variant thereof. The Applicants believe that this full length gene is essential to the growth and/or survival of an organism which possesses it, such as *Streptococcus pneumoniae*.

As a further aspect of the invention there are provided isolated nucleic acid molecules encoding and/or expressing priA polypeptides and polynucleotides, particularly *Streptococcus pneumoniae* priA polypeptides and polynucleotides, including, for example, unprocessed RNAs, ribozyme RNAs, mRNAs, cDNAs, genomic DNAs, B- and Z-DNAs. Further embodiments of the invention include biologically, diagnostically, prophylactically, clinically or therapeutically useful polynucleotides and polypeptides, and variants thereof, and compositions comprising the same.

Another aspect of the invention relates to isolated polynucleotides, including at least one full length gene, that encodes a priA polypeptide having a deduced amino acid sequence of Table 1 [SEQ ID NO:2] and polynucleotides closely related thereto and variants thereof.

In another particularly preferred embodiment of the invention there is a priA polypeptide from *Streptococcus pneumoniae* comprising or consisting of an amino acid sequence of Table 1 [SEQ ID NO:2], or a variant thereof.

Using the information provided herein, such as a polynucleotide sequence set out in Table 1 [SEQ ID NOs:1 or 5], a polynucleotide of the invention encoding priA polypeptide may be obtained using standard cloning and screening methods, such as those for cloning and sequencing chromosomal DNA fragments from bacteria using *Streptococcus pneumoniae* 0100993 cells as starting material, followed by obtaining a full length clone. For example, to obtain a polynucleotide sequence of the invention, such as a polynucleotide sequence given in Table 1 [SEQ ID NOs:1 or 5], typically a library of clones of chromosomal DNA of *Streptococcus pneumoniae* 0100993 in *E. coli* or some other suitable host is probed with a radiolabeled oligonucleotide, preferably a 17-mer or longer, derived from a partial sequence. Clones carrying DNA identical to that of the probe can then be distinguished using stringent hybridization conditions. By sequencing the individual clones thus identified by hybridization with sequencing primers designed from the original polypeptide or polynucleotide sequence it is then possible to extend the polynucleotide sequence in both directions to determine a full length gene sequence. Conveniently, such sequencing is performed, for example, using denatured double stranded DNA prepared from a plasmid clone. Suitable techniques are described by Maniatis, T., Fritsch, E. F. and Sambrook et al., *MOLECULAR CLONING, A LABORATORY MANUAL,* 2nd Ed.; Cold Spring Harbor Laboratory Press, Cold Spring Harbor, N.Y. (1989). (see in particular Screening By Hybridization 1.90 and Sequencing Denatured Double-Stranded DNA Templates 13.70). Direct genomic DNA sequencing may also be performed to obtain a full length gene sequence. Illustrative of the invention, each polynucleotide set out in Table 1 [SEQ ID NOs:1 or 5] was discovered in a DNA library derived from *Streptococcus pneumoniae* 0100993.

Moreover, each DNA sequence set out in Table 1 [SEQ ID NOs:1 or 5] contains an open reading frame encoding a protein having about the number of amino acid residues set forth in Table 1 [SEQ ID NO:2] with a deduced molecular weight that can be calculated using amino acid residue molecular weight values well known to those skilled in the art. The polynucleotide of SEQ ID NO: 1, between nucleotide number 498 and the stop codon which begins at nucleotide number 2910 of SEQ ID NO:1, encodes the polypeptide of SEQ ID NO:2.

In a further aspect, the present invention provides for an isolated polynucleotide comprising or consisting of:

(a) a polynucleotide sequence which has at least 70% identity, preferably at least 80% identity, more preferably at least 90% identity, yet more preferably at least 95% identity, even more preferably at least 97–99% or exact identity to SEQ ID NOs:1 or 5 over the entire length of SEQ ID NOs:1 or 5;

(b) a polynucleotide sequence encoding a polypeptide which has at least 70% identity, preferably at least 80% identity, more preferably at least 90% identity, yet more preferably at least 95% identity, even more preferably at least 97–99% or 100% exact, to the amino acid sequence of SEQ ID NO:2, over the entire length of SEQ ID NO:2.

A polynucleotide encoding a polypeptide of the present invention, including homologs and orthologs from species other than *Streptococcus pneumoniae*, may be obtained by a process which comprises the steps of screening an appropriate library under stringent hybridization conditions with a labeled or detectable probe consisting of or comprising the sequence of SEQ ID NO: 1 or a fragment thereof, and isolating a fill-length gene and/or genomic clones containing said polynucleotide sequence.

The invention provides a polynucleotide sequence identical over its entire length to a coding sequence (open reading frame) in Table 1 [SEQ ID NOs:1 or 5]. Also provided by the invention is a coding sequence for a mature polypeptide or a fragment thereof, by itself as well as a coding sequence for a mature polypeptide or a fragment in reading frame with another coding sequence, such as a sequence encoding a leader or secretory sequence, a pre-, or pro- or prepro-protein sequence. The polynucleotide of the invention may also contain at least one non-coding sequence, including for example, but not limited to at least one non-coding 5' and 3' sequence, such as the transcribed but non-translated sequences, termination signals (such as rho-dependent and rho-independent termination signals), ribosome binding sites, Kozak sequences, sequences that stabilize mRNA, introns, and polyadenylation signals. The polynucleotide sequence may also comprise additional coding sequence encoding additional amino acids. For example, a marker sequence that facilitates purification of the fused polypeptide can be encoded. In certain embodiments of the invention, the marker sequence is a hexa-histidine peptide, as provided in the pQE vector (Qiagen, Inc.) and described in Gentz et al., *Proc. Natl. Acad. Sci., USA* 86: 821–824 (1989), or an HA peptide tag (Wilson et al., *Cell* 37: 767 (1984), both of which may be useful in purifying polypeptide sequence fused to them. Polynucleotides of the invention also include, but are not limited to, polynucleotides comprising a structural gene and its naturally associated sequences that control gene expression.

A preferred embodiment of the invention is a polynucleotide of consisting of or comprising nucleotide 498 to the nucleotide immediately upstream of or including nucleotide 2910 set forth in SEQ ID NO:1 of Table 1, both of which encode the priA polypeptide.

The invention also includes a polynucleotide consisting of or comprising a polynucleotide of the formula:

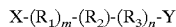

$X\text{-}(R_1)_m\text{-}(R_2)\text{-}(R_3)_n\text{-}Y$ wherein, at the 5' end of the molecule, X is hydrogen, a metal or a modified nucleotide residue, or together with Y defines a covalent bond, and at the 3' end of the molecule, Y is hydrogen, a metal, or a modified nucleotide residue, or together with X defines the covalent bond, each occurrence of $R_1$ and $R_3$ is independently any nucleic acid residue or modified nucleic acid residue, m is an integer between 1 and 3000 or zero, n is an integer between 1 and 3000 or zero, and $R_2$ is a nucleic acid sequence or modified nucleic acid sequence of the invention, particularly a nucleic acid sequence selected from Table 1 or a modified nucleic acid sequence thereof. In the polynucleotide formula above, $R_2$ is oriented so that its 5' end nucleic acid residue is at the left, bound to $R_1$, and its 3' end nucleic acid residue is at the right, bound to $R_3$. Any stretch of nucleic acid residues denoted by either $R_1$ and/or $R_2$, where m and/or n is greater than 1, may be either a heteropolymer or a homopolymer, preferably a heteropolymer. Where, in a preferred embodiment, X and Y together define a covalent bond, the polynucleotide of the above formula is a closed, circular polynucleotide, which can be a double-stranded polynucleotide wherein the formula shows a first strand to which the second strand is complementary. In another preferred embodiment m and/or n is an integer between 1 and 1000. Other preferred embodiments of the invention are provided where m is an integer between 1 and 50, 100 or 500, and n is an integer between 1 and 50, 100, or 500.

It is most preferred that a polynucleotide of the invention is derived from *Streptococcus pneumoniae*, however, it may preferably be obtained from other organisms of the same taxonomic genus. A polynucleotide of the invention may also be obtained, for example, from organisms of the same taxonomic family or order.

The term "polynucleotide encoding a polypeptide" as used herein encompasses polynucleotides that include a sequence encoding a polypeptide of the invention, particularly a bacterial polypeptide and more particularly a polypeptide of the *Streptococcus pneumoniae* priA having an amino acid sequence set out in Table 1 [SEQ ID NO:2]. The term also encompasses polynucleotides that include a single continuous region or discontinuous regions encoding the polypeptide (for example, polynucleotides interrupted by integrated phage, an integrated insertion sequence, an integrated vector sequence, an integrated transposon sequence, or due to RNA editing or genomic DNA reorganization) together with additional regions, that also may contain coding and/or non-coding sequences.

The invention further relates to variants of the polynucleotides described herein that encode variants of a polypeptide having a deduced amino acid sequence of Table 1 [SEQ ID NO:2]. Fragments of a polynucleotides of the invention may be used, for example, to synthesize full-length polynucleotides of the invention.

Further particularly preferred embodiments are polynucleotides encoding priA variants, that have the amino acid sequence of priA polypeptide of Table 1 [SEQ ID NO:2] in which several, a few, 5 to 10, 1 to 5, 1 to 3, 2, 1 or no amino acid residues are substituted, modified, deleted and/or added, in any combination. Especially preferred among these are silent substitutions, additions and deletions, that do not alter the properties and activities of priA polypeptide.

Further preferred embodiments of the invention are polynucleotides that are at least 70% identical over their entire length to a polynucleotide encoding priA polypeptide having an amino acid sequence set out in Table 1 [SEQ ID NO:2], and polynucleotides that are complementary to such polynucleotides. Alternatively, most highly preferred are polynucleotides that comprise a region that is at least 80% identical over its entire length to a polynucleotide encoding priA polypeptide and polynucleotides complementary thereto. In this regard, polynucleotides at least 90% identical over their entire length to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

Preferred embodiments are polynucleotides encoding polypeptides that retain substantially the same biological function or activity as the mature polypeptide encoded by a DNA of Table 1 [SEQ ID NOs:1 or 5].

In accordance with certain preferred embodiments of this invention there are provided polynucleotides that hybridize, particularly under stringent conditions, to priA polynucleotide sequences, such as those polynucleotides in Table 1.

The invention further relates to polynucleotides that hybridize to the polynucleotide sequences provided herein. In this regard, the invention especially relates to polynucleotides that hybridize under stringent conditions to the polynucleotides described herein. As herein used, the terms "stringent conditions" and "stringent hybridization conditions" mean hybridization occurring only if there is at least 95% and preferably at least 97% identity between the sequences. A specific example of stringent hybridization conditions is overnight incubation at 42° C. in a solution comprising: 50% formamide, 5× SSC (150 mM NaCl, 15 mM trisodium citrate), 50 mM sodium phosphate (pH7.6), 5× Denhardt's solution, 10% dextran sulfate, and 20 micrograms/ml of denatured, sheared salmon sperm DNA, followed by washing the hybridization support in 0.1× SSC at about 65° C. Hybridization and wash conditions are well known and exemplified in Sambrook, et al., Molecular Cloning: A Laboratory Manual, Second Edition, Cold Spring Harbor, N.Y., (1989), particularly Chapter 11 therein. Solution hybridization may also be used with the polynucleotide sequences provided by the invention.

The invention also provides a polynucleotide consisting of or comprising a polynucleotide sequence obtained by screening an appropriAte library containing the complete gene for a polynucleotide sequence set forth in SEQ ID NOs:1 or 5 under stringent hybridization conditions with a probe having the sequence of said polynucleotide sequence set forth in SEQ ID NOs:1 or 5 or a fragment thereof; and isolating said polynucleotide sequence. Fragments useful for obtaining such a polynucleotide include, for example, probes and primers fully described elsewhere herein.

As discussed elsewhere herein regarding polynucleotide assays of the invention, for instance, the polynucleotides of the invention, may be used as a hybridization probe for RNA, cDNA and genomic DNA to isolate full-length cDNAs and genomic clones encoding priA and to isolate cDNA and genomic clones of other genes that have a high identity, particularly high sequence identity, to the priA gene. Such probes generally will comprise at least 15 nucleotide residues or base pairs. Preferably, such probes will have at least 30 nucleotide residues or base pairs and may have at least 50 nucleotide residues or base pairs. Particularly preferred probes will have at least 20 nucleotide residues or base pairs and will have less than 30 nucleotide residues or base pairs.

A coding region of a priA gene may be isolated by screening using a DNA sequence provided in Table 1 [SEQ ID NOs:1 or 5] to synthesize an oligonucleotide probe. A labeled oligonucleotide having a sequence complementary to that of a gene of the invention is then used to screen a library of cDNA, genomic DNA or mRNA to determine which members of the library the probe hybridizes to.

There are several methods available and well known to those skilled in the art to obtain full-length DNAs, or extend short DNAs, for example those based on the method of Rapid Amplification of cDNA ends (RACE) (see, for example, Frohman, et al, PNAS USA 85, 8998–9002, 1988). Recent modifications of the technique, exemplified by the Marathon™ technology (Clontech Laboratories Inc.) for example, have significantly simplified the search for longer cDNAs. In the Marathon™ technology, cDNAs have been prepared from mRNA extracted from a chosen tissue and an 'adaptor' sequence ligated onto each end. Nucleic acid amplification (PCR) is then carried out to amplify the "missing" 5' end of the DNA using a combination of gene specific and adaptor specific oligonucleotide primers. The PCR reaction is then repeated using "nested" primers, that is, primers designed to anneal within the amplified product (typically an adaptor specific primer that anneals further 3' in the adaptor sequence and a gene specific primer that anneals further 5' in the known gene sequence). The products of this reaction can then be analyzed by DNA sequencing and a full-length DNA constructed either by joining the product directly to the existing DNA to give a complete sequence, or carrying out a separate full-length PCR using the new sequence information for the design of the 5' primer.

The polynucleotides and polypeptides of the invention may be employed, for example, as research reagents and materials for discovery of treatments of and diagnostics for diseases, particularly human diseases, as further discussed herein relating to polynucleotide assays.

The polynucleotides of the invention that are oligonucleotides derived from a sequence of Table 1 [SEQ ID NOS:1 or 2] may be used in the processes herein as described, but preferably for PCR, to determine whether or not the polynucleotides identified herein in whole or in part are transcribed in bacteria in infected tissue. It is recognized that such sequences will also have utility in diagnosis of the stage of infection and type of infection the pathogen has attained.

The invention also provides polynucleotides that encode a polypeptide that is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may allow protein transport, may lengthen or shorten protein half-life or may facilitate manipulation of a protein for assay or production, among other things. As generally is the case in vivo, the additional amino acids may be processed away from the mature protein by cellular enzymes.

For each and every polynucleotide of the invention there is provided a polynucleotide complementary to it. It is preferred that these complementary polynucleotides are fully complementary to each polynucleotide with which they are complementary.

A precursor protein, having a mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In addition to the standard A, G, C, T/U representations for nucleotides, the term "N" may also be used in describing certain polynucleotides of the invention. "N" means that any of the four DNA or RNA nucleotides may appear at such a designated position in the DNA or RNA sequence, except it is preferred that N is not a nucleic acid that when taken in combination with adjacent nucleotide positions, when read in the correct reading frame, would have the effect of generating a premature termination codon in such reading frame.

In sum, a polynucleotide of the invention may encode a mature protein, a mature protein plus a leader sequence (which may be referred to as a preprotein), a precursor of a mature protein having one or more prosequences that are not the leader sequences of a preprotein, or a preproprotein, which is a precursor to a proprotein, having a leader sequence and one or more prosequences, which generally are removed during processing steps that produce active and mature forms of the polypeptide.

Vectors, Host Cells, Expression Systems

The invention also relates to vectors that comprise a polynucleotide or polynucleotides of the invention, host cells that are genetically engineered with vectors of the invention and the production of polypeptides of the invention by recombinant techniques. Cell-free translation systems can also be employed to produce such proteins using RNAs derived from the DNA constructs of the invention.

Recombinant polypeptides of the present invention may be prepared by processes well known in those skilled in the art from genetically engineered host cells comprising expression systems. Accordingly, in a further aspect, the present invention relates to expression systems which comprise a polynucleotide or polynucleotides of the present invention, to host cells which are genetically engineered with such expression systems, and to the production of polypeptides of the invention by recombinant techniques.

For recombinant production of the polypeptides of the invention, host cells can be genetically engineered to incorporate expression systems or portions thereof or polynucleotides of the invention. Introduction of a polynucleotide into the host cell can be effected by methods described in many standard laboratory manuals, such as Davis, et al., *BASIC METHODS IN MOLECULAR BIOLOGY*, (1986) and Sambrook, et al., *MOLECULAR CLONING: A LABORATORY MANUAL*, 2nd Ed., Cold Spring Harbor Laboratory Press, Cold Spring Harbor, N.Y. (1989), such as, calcium phosphate transfection, DEAE-dextran mediated transfection, transvection, microinjection, cationic hpid-mediated transfection, electroporation, transduction, scrape loading, ballistic introduction and infection.

Representative examples of appropriAte hosts include bacterial cells, such as cells of streptococci, staphylococci, enterococci *E. coli*, streptomyces, cyanobacteria, *Bacillus subtilis*, and *Streptococcus pneumoniae*; fungal cells, such as cells of a yeast, Kluveromyces, Saccharomyces, a basidiomycete, *Candida albicans* and Aspergillus; insect cells such as cells of Drosophila S2 and Spodoptera Sf9; animal cells such as CHO, COS, HeLa, C127, 3T3, BHK, 293, CV-1 and Bowes melanoma cells; and plant cells, such as cells of a gymnosperm or angiosperm.

A great variety of expression systems can be used to produce the polypeptides of the invention. Such vectors include, among others, chromosomal-, episomal- and virus-derived vectors, for example, vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses, picomaviruses and retroviruses, and vectors derived from combinations thereof; such as those derived from plasmid and bacteriophage genetic elements, such as cosmids and phagemids. The expression system constructs may contain control regions that regulate as well as engender expression. Generally, any system or vector suitable to maintain, propagate or express polynucleotides and/or to express a polypeptide in a host may be used for expression in this regard. The appropriate DNA sequence may be inserted into the expression system by any of a variety of well-known and routine techniques, such as, for example, those set forth in Sambrook et al., *MOLECULAR CLONING, A LABORATORY MANUAL*, (supra).

In recombinant expression systems in eukaryotes, for secretion of a translated protein into the lumen of the endoplasmic reticulum, into the periplasmic space or into the extracellular environment, appropriate secretion signals may be incorporated into the expressed polypeptide. These signals may be endogenous to the polypeptide or they may be heterologous signals.

Polypeptides of the invention can be recovered and purified from recombinant cell cultures by well-known methods including ammonium sulfate or ethanol precipitation, acid action, anion or cation exchange chromatography, phosphocellulose chromatography, hydrophobic interaction chromatography, affinity chromatography, hydroxylapatite chromatography, and lectin chromatography. Most preferably, high performance liquid chromatography is employed for purification. Well known techniques for refolding protein may be employed to regenerate active conformation when the polypeptide is denatured during isolation and or purification.

Diagnostic, Prognostic, Serotyping and Mutation Assays

This invention is also related to the use of priA polynucleotides and polypeptides of the invention for use as diagnostic reagents. Detection of priA polynucleotides and/or polypeptides in a eukaryote, particularly a mammal, and especially a human, will provide a diagnostic method for diagnosis of disease, staging of disease or response of an infectious organism to drugs. Eukaryotes, particularly mammals, and especially humans, particularly those infected or suspected to be infected with an organism comprising the priA gene or protein, may be detected at the nucleic acid or amino acid level by a variety of well known techniques as well as by methods provided herein.

Polypeptides and polynucleotides for prognosis, diagnosis or other analysis may be obtained from a putatively infected and/or infected individual's bodily materials. Polynucleotides from any of these sources, particularly DNA or RNA, may be used directly for detection or may be amplified enzymatically by using PCR or any other amplification technique prior to analysis. RNA, particularly mRNA, cDNA and genomic DNA may also be used in the same ways. Using amplification, characterization of the species and strain of infectious or resident organism present in an individual, may be made by an analysis of the genotype of a selected polynucleotide of the organism. Deletions and insertions can be detected by a change in size of the amplified product in comparison to a genotype of a reference sequence selected from a related organism, preferably a different species of the same genus or a different strain of the same species. Point mutations can be identified by hybridizing amplified DNA to labeled priA polynucleotide sequences. Perfectly or significantly matched sequences can be distinguished from imperfectly or more significantly mismatched duplexes by DNase or RNase digestion, for DNA or RNA respectively, or by detecting differences in melting temperatures or renaturation kinetics. Polynucleotide sequence differences may also be detected by alterations in the electrophoretic mobility of polynucleotide fragments in gels as compared to a reference sequence. This may be carried out with or without denaturing agents. Polynucleotide differences may also be detected by direct DNA or RNA sequencing. See, for example, Myers et al., *Science*, 230: 1242 (1985). Sequence changes at specific locations also may be revealed by nuclease protection assays, such as Rnase, V1 and S1 protection assay or a chemical cleavage method. See, for example, Cotton et al., *Proc. Natl. Acad. Sci., USA*, 85: 4397–4401 (1985).

In another embodiment, an array of oligonucleotides probes comprising priA nucleotide sequence or fragments thereof can be constructed to conduct efficient screening of, for example, genetic mutations, serotype, taxonomic classification or identification. Array technology methods are well known and have general applicability and can be used to address a variety of questions in molecular genetics including gene expression, genetic linkage, and genetic variability (see, for example, Chee et al., *Science*, 274: 610 (1996)).

Thus in another aspect, the present invention relates to a diagnostic kit which comprises:

(a) a polynucleotide of the present invention, preferably the nucleotide sequence of SEQ ID NO: 1, or a fragment thereof;

(b) a nucleotide sequence complementary to that of (a);

(c) a polypeptide of the present invention, preferably the polypeptide of SEQ ID NO:2 or a fragment thereof; or (d) an antibody to a polypeptide of the present invention, preferably to the polypeptide of SEQ ID NO:2.

It will be appreciated that in any such kit, (a), (b), (c) or (d) may comprise a substantial component. Such a kit will be of use in diagnosing a disease or susceptibility to a Disease, among others.

This invention also relates to the use of polynucleotides of the present invention as diagnostic reagents. Detection of a mutated form of a polynucleotide of the invention, preferable, SEQ ID NOs:1 or 5, which is associated with a disease or pathogenicity will provide a diagnostic tool that can add to, or define, a diagnosis of a disease, a prognosis of a course of disease, a determination of a stage of disease, or a susceptibility to a disease, which results from under-expression, over-expression or altered expression of the polynucleotide. Organisms, particularly infectious organisms, carrying mutations in such polynucleotide may be detected at the polynucleotide level by a variety of techniques, such as those described elsewhere herein.

The nucleotide sequences of the present invention are also valuable for organism chromosome identification. The sequence is specifically targeted to, and can hybridize with, a particular location on an organism's chromosome, particularly to a Streptococcus pneumoniae chromosome. The mapping of relevant sequences to chromosomes according to the present invention may be an important step in correlating those sequences with pathogenic potential and/or an ecological niche of an organism and/or drug resistance of an organism, as well as the essentiality of the gene to the organism. Once a sequence has been mapped to a precise chromosomal location, the physical position of the sequence on the chromosome can be correlated with genetic map data. Such data may be found on-line in a sequence database. The relationship between genes and diseases that have been mapped to the same chromosomal region are then identified through known genetic methods, for example, through linkage analysis (coinheritance of physically adjacent genes) or mating studies, such as by conjugation.

The differences in a polynucleotide and/or polypeptide sequence between organisms possessing a first phenotype and organisms possessing a different, second different phenotype can also be determined. If a mutation is observed in some or all organisms possessing the first phenotype but not in any organisms possessing the second phenotype, then the mutation is likely to be the causative agent of the first phenotype.

Cells from an organism carrying mutations or polymorphisms (allelic variations) in a polynucleotide and/or polypeptide of the invention may also be detected at the polynucleotide or polypeptide level by a variety of techniques, to allow for serotyping, for example. For example, RT-PCR can be used to detect mutations in the RNA. It is particularly preferred to use RT-PCR in conjunction with automated detection systems, such as, for example, GeneScan. RNA, cDNA or genomic DNA may also be used for the same purpose, PCR. As an example, PCR primers complementary to a polynucleotide encoding priA polypeptide can be used to identify and analyze mutations. Examples of representative primers are shown below in Table 2.

TABLE 2

Primers for amplification of priA polynucleotides

| SEQ ID NO | PRIMER SEQUENCE |
|---|---|
| 3 | 5'-GTGAAGCAGTGCGTCGCCGTATCGAAG-3' |
| 4 | 5'-ACCATGAGCCGCAGCAATTTTTATAAGAAG-3' |

The invention also includes primers of the formula:

$$X\text{-}(R_1)_m\text{-}(R_2)\text{-}(R_3)_n\text{-}Y$$

wherein, at the 5' end of the molecule, X is hydrogen, a metal or a modified nucleotide residue, and at the 3' end of the molecule, Y is hydrogen, a metal or a modified nucleotide residue, $R_1$ and $R_3$ are any nucleic acid residue or modified nucleotide residue, m is an integer between 1 and 20 or zero, n is an integer between 1 and 20 or zero, and $R_2$ is a primer sequence of the invention, particularly a primer sequence selected from Table 2. In the polynucleotide formula above $R_2$ is oriented so that its 5' end nucleotide residue is at the left, bound to $R_1$, and its 3' end nucleotide residue is at the right, bound to $R_3$. Any stretch of nucleic acid residues denoted by either R group, where m and/or n is greater than 1, may be either a heteropolymer or a homopolymer, preferably a heteropolymer being complementary to a region of a polynucleotide of Table 1. In a preferred embodiment m and/or n is an integer between 1 and 10.

The invention further provides these primers with 1, 2, 3 or 4 nucleotides removed from the 5' and/or the 3' end. These primers may be used for, among other things, amplifying priA DNA and/or RNA isolated from a sample derived from an individual, such as a bodily material. The primers may be used to amplify a polynucleotide isolated from an infected individual, such that the polynucleotide may then be subject to various techniques for elucidation of the polynucleotide sequence. In this way, mutations in the polynucleotide sequence may be detected and used to diagnose and/or prognose the infection or its stage or course, or to serotype and/or classify the infectious agent.

The invention further provides a process for diagnosing, disease, preferably bacterial infections, more preferably infections caused by Streptococcus pneumoniae, comprising determining from a sample derived from an individual, such as a bodily material, an increased level of expression of polynucleotide having a sequence of Table 1 [SEQ ID NO: 1]. Increased or decreased expression of a priA polynucleotide can be measured using any on of the methods well known in the art for the quantitation of polynucleotides, such as, for example, amplification, PCR, RT-PCR, RNase protection, Northern blotting, spectrometry and other hybridization methods.

In addition, a diagnostic assay in accordance with the invention for detecting over-expression of priA polypeptide compared to normal control tissue samples may be used to detect the presence of an infection, for example. Assay techniques that can be used to determine levels of a priA polypeptide, in a sample derived from a host, such as a bodily material, are well-known to those of skill in the art. Such assay methods include radioimmunoassays, competitive-binding assays, Western Blot analysis, antibody sandwich assays, antibody detection and ELISA assays.

Differential Expression

The polynucleotides and polynucleotides of the invention may be used as reagents for differential screening methods. There are many differential screening and differential display methods known in the art in which the polynucleotides and polypeptides of the invention may be used. For example, the differential display technique is described by Chuang et al., *J. Bacteriol.* 175:2026–2036 (1993). This method identifies those genes which are expressed in an organism by identifying mRNA present using randomly-primed RT-PCR. By comparing pre-infection and post infection profiles, genes up and down regulated during infection can be identified and the RT-PCR product sequenced and matched to ORF "unknowns."

In Vivo Expression Technology (VET) is described by Camilli et al., *Proc. Nat'l Acad. Sci. USA.* 91:2634–2638 (1994). IVET identifies genes up-regulated during infection when compared to laboratory cultivation, implying an important role in infection. ORFs identified by this technique are implied to have a significant role in infection establishment and/or maintenance. In this technique random chromosomal fragments of target organism are cloned upstream of a promoter-less recombinase gene in a plasmid vector. This construct is introduced into the target organism which carries an antibiotic resistance gene flanked by resolvase sites. Growth in the presence of the antibiotic removes from the population those fragments cloned into the plasmid vector capable of supporting transcription of the recombinase gene and therefore have caused loss of antibiotic resistance. The resistant pool is introduced into a host and at various times after infection bacteria may be recovered and assessed for the presence of antibiotic resistance. The chromosomal fragment carried by each antibiotic sensitive bacterium should carry a promoter or portion of a gene normally upregulated during infection. Sequencing upstream of the recombinase gene allows identification of the up regulated gene.

RT-PCR may also be used to analyze gene expression patterns. For RT PCR using the polynucleotides of the invention, messenger RNA is isolated from bacterial infected tissue, e.g., 48 hour murine lung infections, and the amount of each mRNA species assessed by reverse transcription of the RNA sample primed with random hexanucleotides followed by PCR with gene specific primer pairs. The determination of the presence and amount of a particular mRNA species by quantification of the resultant PCR product provides information on the bacterial genes which are transcribed in the infected tissue. Analysis of gene transcription can be carried out at different times of infection to gain a detailed knowledge of gene regulation in bacterial pathogenesis allowing for a clearer understanding of which gene products represent targets for screens for antibacterials. Because of the gene specific nature of the PCR primers employed it should be understood that the bacterial mRNA preparation need not be free of mammalian RNA. This allows the investigator to carry out a simple and quick RNA preparation from infected tissue to obtain bacterial mRNA species which are very short lived in the bacterium (in the order of 2 minute halflives). Optimally the bacterial mRNA is prepared from infected murine lung tissue by mechanical disruption in the presence of TRIzole (GIBCO-BRL) for very short periods of time, subsequent processing according to the manufacturers of TRIzole reagent and DNAase treatment to remove contaminating DNA. Preferably the process is optimized by finding those conditions which give a maximum amount of Streptococcus pneumoniae 16S ribosomal RNA as detected by probing Northerns with a suitably labeled sequence specific oligonucleotide probe. Typically a 5' dye labeled primer is used in each PCR primer pair in a PCR reaction which is terminated optimally between 8 and 25 cycles. The PCR products are separated on 6% polyacrylamide gels with detection and quantification using GeneScanner (manufactured by ABI).

Gridding and Polynucleotide Subtraction

Methods have been described for obtaining information about gene expression and identity using so called "high density DNA arrays" or grids. See, e.g., M. Chee et al., Science 274:610–614 (1996) and other references cited therein. Such gridding assays have been employed to identify certain novel gene sequences, referred to as Expressed Sequence Tags (EST) (Adams et a., Science 252:1651–1656 (1991)). A variety of techniques have also been described for identifying particular gene sequences on the basis of their gene products. For example, see International Patent Application No. WO91/07087, published May 30, 1991. In addition, methods have been described for the amplification of desired sequences. For example, see International Patent Application No. WO91117271, published Nov. 14, 1991.

The polynucleotides of the invention may be used as components of polynucleotide arrays, preferably high density arrays or grids. These high density arrays are particularly useful for diagnostic and prognostic purposes. For example, a set of spots each comprising a different gene, and further comprising a polynucleotide or polynucleotides of the invention, may be used for probing, such as using hybridization or nucleic acid amplification, using a probes obtained or derived from a bodily sample, to determine the presence of a particular polynucleotide sequence or related sequence in an individual. Such a presence may indicate the presence of a pathogen, particularly Streptococcus pneumoniae, and may be useful in diagnosing and/or prognosing disease or a course of disease. A grid comprising a number of variants of the polynucleotide sequence of SEQ ID NOs: 1 or 5 are preferred. Also preferred is a comprising a number of variants of a polynucleotide sequence encoding the polypeptide sequence of SEQ ID NO:2.

Antibodies

The polypeptides and polynucleotides of the invention or variants thereof, or cells expressing the same can be used as immunogens to produce antibodies immunospecific for such polypeptides or polynucleotides respectively.

In certain preferred embodiments of the invention there are provided antbodies against priA polypeptides or polynucleotides.

Antibodies generated against the polypeptides or polynucleotides of the invention can be obtained by administering the polypeptides and/or polynucleotides of the invention, or epitope-bearing fragments of either or both, analogues of either or both, or cells expressing either or both, to an animal, preferably a nonhuman, using routine protocols. For preparation of monoclonal antibodies, any technique known in the art that provides antibodies produced by continuous cell line cultures can be used. Examples include various techniques, such as those in Kohler, G. and Milstein, C., Nature 256: 495–497 (1975); Kozbor et al., Immunology Today 4: 72 (1983); Cole et al., pg. 77–96 in MONOCLONAL ANTIBODIES AND CANCER THERAPY, Alan R. Liss, Inc. (1985).

Techniques for the production of single chain antibodies (U.S. Pat. No. 4,946,778) can be adapted to produce single chain antibodies to polypeptides or polynucleotides of this invention. Also, transgenic mice, or other organisms such as other mammals, may be used to express humanized antibodies immunospecific to the polypeptides or polynucleotides of the invention.

Alternatively, phage display technology may be utilized to select antibody genes with binding activities towards a polypeptide of the invention either from repertoires of PCR amplified v-genes of lymphocytes from humans screened for possessing anti-priA or from naive libraries (McCafferty, et al, (1990), Nature 348, 552–554; Marks, et al., (1992) Biotechnology 10, 779–783). The affinity of these antibodies can also be improved by, for example, chain shuffling (Clackson et al., (1991) Nature 352: 628).

The above-described antibodies may be employed to isolate or to identify clones expressing the polypeptides or polynucleotides of the invention to purify the polypeptides or polynucleotides by, for example, affinity chromatography.

Thus, among others, antibodies against priA-polypeptide or priA-polynucleotide may be employed to treat infections, particularly bacterial infections.

Polypeptide variants include antigenically, epitopically or immunologically equivalent variants form a particular aspect of this invention.

A polypeptide or polynucleotide of the invention, such as an antigenically or immunologically equivalent derivative or a fusion protein of the polypeptide is used as an antigen to immunize a mouse or other animal such as a rat or chicken. The fusion protein may provide stability to the polypeptide. The antigen may be associated, for example by conjugation, with an immunogenic carrier protein for example bovine serum albumin, keyhole limpet haemocyanin or tetanus toxoid. Alternatively, a multiple antigenic polypeptide comprising multiple copies of the polypeptide, or an antigenically or immunologically equivalent polypeptide thereof may be sufficiently antigenic to improve immunogenicity so as to obviate the use of a carrier.

Preferably, the antibody or variant thereof is modified to make it less immunogenic in the individual. For example, if the individual is human the antibody may most preferably be "humanized," where the complimentarity determining region or regions of the hybridoma-derived antibody has been transplanted into a human monoclonal antibody, for example as described in Jones et al. (1986), Nature 321, 522–525 or Tempest et al., (1991) Biotechnology 9, 266–273.

In accordance with an aspect of the invention, there is provided the use of a polynucleotide of the invention for therapeutic or prophylactic purposes, in particular genetic immunization. Among the particularly preferred embodiments of the invention are naturally occurring allelic variants of priA polynucleotides and polypeptides encoded thereby.

The use of a polynucleotide of the invention in genetic immunization will preferably employ a suitable delivery method such as direct injection of plasmid DNA into muscles (Wolff et al., Hum Mol Genet (1992) 1: 363, Manthorpe et al., Hum. Gene Ther. (1983) 4: 419), delivery of DNA complexed with specific protein carriers (Wu et al., J Biol Chem. (1989) 264: 16985), coprecipitation of DNA with calcium phosphate (Benvenisty & Reshef, PNAS USA, (1986) 83: 9551), encapsulation of DNA in various forms of liposomes (Kaneda et al., Science (1989) 243: 375), particle bombardment (Tang et al., Nature (1992) 356:152, Eisenbraun et al., DNA Cell Biol (1993) 12: 791) and in vivo infection using cloned retroviral vectors (Seeger et al., PNAS USA (1984) 81: 5849).

Antagonists and Agonists—Assays and Molecules

Polypeptides and polynucleotides of the invention may also be used to assess the binding of small molecule substrates and ligands in, for example, cells, cell-free preparations, chemical libraries, and natural product mixtures. These substrates and ligands may be natural substrates and ligands or may be strctural or functional mimetics. See, e.g., Coligan et al., Current Protocols in Immunology 1(2): Chapter 5 (1991).

Polypeptides and polynucleotides of the present invention are responsible for many biological functions, including many disease states, in particular the Diseases hereinbefore mentioned. It is therefore desirable to devise screening methods to identify compounds which stimulate or which inhibit the function of the polypeptide or polynucleotide. Accordingly, in a further aspect, the present invention provides for a method of screening compounds to identify those which stimulate or which inhibit the function of a polypeptide or polynucleotide of the invention, as well as related polypeptides and polynucleotides. In general, agonists or antagonists may be employed for therapeutic and prophylactic purposes for such Diseases as hereinbefore mentioned. Compounds may be identified from a variety of sources, for example, cells, cell-free preparations, chemical libraries, and natural product mixtures. Such agonists, antagonists or inhibitors so-identified may be natural or modified substrates, ligands, receptors, enzymes, etc., as the case may be, of priA polypeptides and polynucleotides; or may be structural or functional mimetics thereof (see Coligan et al., Current Protocols in Immunology 1(2):Chapter 5 (1991)).

The screening methods may simply measure the binding of a candidate compound to the polypeptide or polynucleotide, or to cells or membranes bearing the polypeptide or polynucleotide, or a fusion protein of the polypeptide by means of a label directly or indirectly associated with the candidate compound. Alternatively, the screening method may involve competition with a labeled competitor. Further, these screening methods may test whether the candidate compound results in a signal generated by activation or inhibition of the polypeptide or polynucleotide, using detection systems appropriate to the cells comprising the polypeptide or polynucleotide. Inhibitors of activation are generally assayed in the presence of a known agonist and the effect on activation by the agonist by the presence of the candidate compound is observed. Constitutively active polypeptide and/or constitutively expressed polypeptides and polynucleotides may be employed in screening methods for inverse agonists or inhibitors, in the absence of an agonist or inhibitor, by testing whether the candidate compound results in inhibition of activation of the polypeptide or polynucleotide, as the case may be. Further, the screening methods may simply comprise the steps of mixing a candidate compound with a solution containing a polypeptide or polynucleotide of the present invention, to form a mixture, measuring priA polypeptide and/or polynucleotide activity in the mixture, and comparing the priA polypeptide and/or polynucleotide activity of the mixture to a standard. Fusion proteins, such as those made from Fc portion and priA polypeptide, as hereinbefore described, can also be used for high-throughput screening assays to identify antagonists of the polypeptide of the present invention, as well as of phylogenetically and and/or functionally related polypeptides (see D. Bennett et al., J Mol Recognition, 8:52–58 (1995); and K. Johanson et al., J Biol Chem, 270(16):9459–9471 (1995)).

The polynucleotides, polypeptides and antibodies that bind to and/or interact with a polypeptide of the present invention may also be used to configure screening methods for detecting the effect of added compounds on the production of mRNA and/or polypeptide in cells. For example, an ELISA assay may be constructed for measuring secreted or cell associated levels of polypeptide using monoclonal and polyclonal antibodies by standard methods known in the art. This can be used to discover agents which may inhibit or enhance the production of polypeptide (also called antagonist or agonist, respectively) from suitably manipulated cells or tissues.

The invention also provides a method of screening compounds to identify those which enhance (agonist) or block (antagonist) the action of priA polypeptides or polynucleotides, particularly those compounds that are bacteriostatic and/or bactericidal. The method of screening may involve high-throughput techniques. For example, to screen for agonists or antagonists, a synthetic reaction mix, a cellular compartment, such as a membrane, cell envelope or cell wall, or a preparation of any thereof, comprising priA polypeptide and a labeled substrate or ligand of such polypeptide is incubated in the absence or the presence of a candidate molecule that may be a priA agonist or antagonist. The ability of the candidate molecule to agonize or antagonize the priA polypeptide is reflected in decreased binding of the labeled ligand or decreased production of product from such substrate. Molecules that bind gratuitously, i.e., without inducing the effects of priA polypeptide are most likely to be good antagonists. Molecules that bind well and, as the case may be, increase the rate of product production from substrate, increase signal transduction, or increase chemical channel activity are agonists. Detection of the rate or level of, as the case may be, production of product from substrate, signal transduction, or chemical channel activity may be enhanced by using a reporter system. Reporter systems that may be useful in this regard include but are not limited to colorimetric, labeled substrate converted into product, a reporter gene that is responsive to changes in priA polynucleotide or polypeptide activity, and binding assays known in the art.

Polypeptides of the invention may be used to identify membrane bound or soluble receptors, if any, for such polypeptide, through standard receptor binding techniques known in the art. These techniques include, but are not limited to, ligand binding and crosslinking assays in which the polypeptide is labeled with a radioactive isotope (for instance, $^{125}$I), chemically modified (for instance, biotinylated), or fused to a peptide sequence suitable for detection or purification, and incubated with a source of the putative receptor (e.g., cells, cell membranes, cell supernatants, tissue extracts, bodily materials). Other methods include biophysical techniques such as surface plasmon resonance and spectroscopy. These screening methods may also be used to identify agonists and antagonists of the polypeptide which compete with the binding of the polypeptide to its receptor(s), if any. Standard methods for conducting such assays are well understood in the art.

In other embodiments of the invention there are provided methods for identifying compounds which bind to or otherwise interact with and inhibit or activate an activity or expression of a polypeptide and/or polynucleotide of the invention comprising: contacting a polypeptide and/or polynucleotide of the invention with a compound to be screened under conditions to permit binding to or other interaction between the compound and the polypeptide and/or polynucleotide to assess the binding to or other interaction with the compound, such binding or interaction preferably being associated with a second component capable of providing a detectable signal in response to the binding or interaction of the polypeptide and/or polynucleotide with the compound; and determining whether the compound binds to or otherwise interacts with and activates or inhibits an activity or expression of the polypeptide and/or polynucleotide by detecting the presence or absence of a signal generated from the binding or interaction of the compound with the polypeptide and/or polynucleotide.

Another example of an assay for priA agonists is a competitive assay that combines priA and a potential agonist with priA-binding molecules, recombinant priA binding molecules, natural substrates or ligands, or substrate or ligand mimetics, under appropriate conditions for a competitive inhibition assay. PriA can be labeled, such as by radioactivity or a colorimetric compound, such that the number of priA molecules bound to a binding molecule or converted to product can be determined accurately to assess the effectiveness of the potential antagonist.

Potential antagonists include, among others, small organic molecules, peptides, polypeptides and antibodies that bind to a polynucleotide and/or polypeptide of the invention and thereby inhibit or extinguish its activity or expression. Potential antagonists also may be small organic molecules, a peptide, a polypeptide such as a closely related protein or antibody that binds the same sites on a binding molecule, such as a binding molecule, without inducing priA-induced activities, thereby preventing the action or expression of priA polypeptides and/or polynucleotides by excluding priA polypeptides and/or polynucleotides from binding.

Potential antagonists include a small molecule that binds to and occupies the binding site of the polypeptide thereby preventing binding to cellular binding molecules, such that normal biological activity is prevented. Examples of small molecules include but are not limited to small organic molecules, peptides or peptide-like molecules. Other potential antagonists include antisense molecules (see Okano, *J. Neurochem.* 56: 560 (1991); *OLIGODEOXYNUCLEOTIDES AS ANTISENSE INHIBITORS OF GENE EXPRESSION*, CRC Press, Boca Raton, Fla. (1988), for a description of these molecules). Preferred potential antagonists include compounds related to and variants of priA. Other examples of potential polypeptide antagonists include antibodies or, in some cases, oligonucleotides or proteins which are closely related to the ligands, substrates, receptors, enzymes, etc., as the case may be, of the polypeptide, e.g., a fragment of the ligands, substrates, receptors, enzymes, etc.; or small molecules which bind to the polypeptide of the present invention but do not elicit a response, so that the activity of the polypeptide is prevented.

Certain of the polypeptides of the invention are biomimetics, functional mimetics of the natural priA polypeptide. These functional mimetics may be used for, among other things, antagonizing the activity of priA polypeptide or as a antigen or immunogen in a manner described elsewhere herein. Functional mimetics of the polypeptides of the invention include but are not limited to truncated polypeptides. For example, preferred functional mimetics include, a polypeptide comprising the polypeptide sequence set forth in SEQ ID NO:2 lacking 20, 30, 40, 50, 60, 70 or 80 amino- or carboxy-terminal amino acid residues, including fusion proteins comprising one or more of these truncated sequences. Polynucleotides encoding each of these functional mimetics may be used as expression cassettes to express each mimetic polypeptide. It is preferred that these cassettes comprise 5' and 3' restriction sites to allow for a convenient means to ligate the cassettes together when desired. It is further preferred that these cassettes comprise gene expression signals known in the art or described elsewhere herein.

Thus, in another aspect, the present invention relates to a screening kit for identifying agonists, antagonists, ligands, receptors, substrates, enzymes, etc. for a polypeptide and/or polynucleotide of the present invention; or compounds which decrease or enhance the production of such polypeptides and/or polynucleotides, which comprises:

(a) a polypeptide and/or a polynucleotide of the present invention;

(b) a recombinant cell expressing a polypeptide and/or polynucleotide of the present invention;

(c) a cell membrane expressing a polypeptide and/or polynucleotide of the present invention; or (d) antibody to a polypeptide and/or polynucleotide of the present invention; which polypeptide is preferably that of SEQ ID NO:2, and which polynucleotide is preferably that of SEQ ID NOs:1 or 5.

It will be appreciated that in any such kit, (a), (b), (c) or (d) may comprise a substantial component.

It will be readily appreciated by the skilled artisan that a polypeptide and/or polynucleotide of the present invention may also be used in a method for the structure-based design of an agonist, antagonist or inhibitor of the polypeptide and/or polynucleotide, by:

(a) determining in the first instance the three-dimensional structure of the polypeptide and/or polynucleotide, or complexes thereof;

(b) deducing the three-dimensional structure for the likely reactive site(s), binding site(s) or motif(s) of an agonist, antagonist or inhibitor;

(c) synthesizing candidate compounds that are predicted to bind to or react with the deduced binding site(s), reactive site(s), and/or motif(s); and (d) testing whether the candidate compounds are indeed agonists, antagonists or inhibitors.

It will be further appreciated that this will normally be an iterative process, and this iterative process may be performed using automated and computer-controlled steps.

In a further aspect, the present invention provides methods of treating abnormal conditions such as, for instance, a Disease, related to either an excess of, an under-expression of, an elevated activity of; or a decreased activity of priA polypeptide and/or polynucleotide.

If the expression and/or activity of the polypeptide and/or polynucleotide is in excess, several approaches are available. One approach comprises administering to an individual in need thereof an inhibitor compound (antagonist) as herein described, optionally in combination with a pharmaceutically acceptable carrier, in an amount effective to inhibit the function and/or expression of the polypeptide and/or polynucleotide, such as, for example, by blocking the binding of ligands, substrates, receptors, enzymes, etc., or by inhibiting a second signal, and thereby alleviating the abnormal condition. In another approach, soluble forms of the polypeptides still capable of binding the ligand, substrate, enzymes, receptors, etc. in competition with endogenous polypeptide and/or polynucleotide may be administered. Typical examples of such competitors include fragments of the priA polypeptide and/or polypeptide.

In a further aspect, the present invention relates to genetically engineered soluble fusion proteins comprising a polypeptide of the present invention, or a fragment thereof, and various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simply by incorporation of a cleavage sequence which can be cleaved with blood clotting factor Xa. Furthermore, this invention relates to processes for the preparation of these fusion proteins by genetic engineering, and to the use thereof for drug screening, diagnosis and therapy. A further aspect of the invention also relates to polynucleotides encoding such fusion proteins. Examples of fusion protein technology can be found in International Patent Application Nos. WO94/29458 and WO94/22914.

In still another approach, expression of the gene encoding endogenous priA polypeptide can be inhibited using expression blocking techniques. This blocking may be targeted against any step in gene expression, but is preferably targeted against transcription and/or translation. An examples of a known technique of this sort involve the use of antisense sequences, either internally generated or separately administered (see, for example, O'Connor, *J Neurochem* (1991) 56:560 in Oligodeoxynucleotides as Antisense Inhibitors of Gene Expression, CRC Press, Boca Raton, Fla. (1988)). Alternatively, oligonucleotides which form triple helices with the gene can be supplied (see, for example, Lee et al., *Nucleic Acids Res* (1979) 6:3073; Cooney et al., *Science* (1988) 241:456; Dervan et al., *Science* (1991) 251:1360). These oligomers can be administered per se or the relevant oligomers can be expressed in vivo.

Each of the polynucleotide sequences provided herein may be used in the discovery and development of antibacterial compounds. The encoded protein, upon expression, can be used as a target for the screening of antibacterial drugs. Additionally, the polynucleotide sequences encoding the amino terminal regions of the encoded protein or Shine-Delgamo or other translation facilitating sequences of the respective mRNA can be used to construct antisense sequences to control the expression of the coding sequence of interest.

The invention also provides the use of the polypeptide, polynucleotide, agonist or antagonist of the invention to interfere with the initial physical interaction between a pathogen or pathogens and a eukaryotic, preferably mammalian, host responsible for sequelae of infection. In particular, the molecules of the invention may be used: in the prevention of adhesion of bacteria, in particular gram positive and/or gram negative bacteria, to eukaryotic, preferably mammalian, extracellular matrix proteins on in-dwelling devices or to extracellular matrix proteins in wounds; to block priA protein-mediated mammalian cell invasion by, for example, initiating phosphorylation of mammalian tyrosine kinases (Rosenshine et al., *Infect. Immun.* 60:2211 (1992); to block bacterial adhesion between eukaryotic, preferably mammalian, extracellular matrix proteins and bacterial priA proteins that mediate tissue damage and/or; to block the normal progression of pathogenesis in infections initiated other than by the implantation of in-dwelling devices or by other surgical techniques.

In accordance with yet another aspect of the invention, there are provided priA agonists and antagonists, preferably bacteriostatic or bacteriocidal agonists and antagonists.

The antagonists and agonists of the invention may be employed, for instance, to prevent, inhibit and/or treat diseases.

*Helicobacter pylori* (herein "*H. pylori*") bacteria infect the stomachs of over one-third of the world's population causing stomach cancer, ulcers, and gastritis (International Agency for Research on Cancer (1994) *Schistosomes, Liver Flukes and Helicobacter Pylori* (International Agency for Research on Cancer, Lyon, France. Moreover, the International Agency for Research on Cancer recently recognized a cause-and-effect relationship between *H. pylori* and gastric adenocarcinoma, classifying the bacterium as a Group I (definite) carcinogen. Preferred antimicrobial compounds of the invention (agonists and antagonists of priA polypeptides and/or polynucleotides) found using screens provided by the invention, or known in the art, particularly narrow-spectrum antibiotics, should be useful in the treatment of *H. pylori* infection. Such treatment should decrease the advent of *H. pylori*-induced cancers, such as gastrointestinal carcinoma. Such treatment should also prevent inhibit and/or cure gastric ulcers and gastritis.

Vaccines

There are provided by the invention, products, compositions and methods for assessing priA expression, treating disease, assaying genetic variation, and administering a priA polypeptide and/or polynucleotide to an organism to raise an immunological response against a bacteria, especially a *Streptococcus pneumoniae* bacteria.

Another aspect of the invention relates to a method for inducing an immunological response in an individual, particularly a mammal which comprises inoculating the individual with priA polynucleotide and/or polypeptide, or a fragment or variant thereof, adequate to produce antibody and/or T cell immune response to protect said individual from infection, particularly bacterial infection and most particularly *Streptococcus pneumoniae* infection. Also provided are methods whereby such immunological response slows bacterial replication. Yet another aspect of the invention relates to a method of inducing immunological response in an individual which comprises delivering to such individual a nucleic acid vector, sequence or ribozyme to direct expression of priA polynucleotide and/or polypeptide, or a fragment or a variant thereof, for expressing priA polynucleotide and/or polypeptide, or a fragment or a variant thereof in vivo in order to induce an immunological response, such as, to produce antibody and/or T cell immune response, including, for example, cytokine-producing T cells or cytotoxic T cells, to protect said individual, preferably a human, from disease, whether that disease is already established within the individual or not. One example of administering the gene is by accelerating it into the desired cells as a coating on particles or otherwise. Such nucleic acid vector may comprise DNA, RNA, a ribozyme, a modified nucleic acid, a DNA/RNA hybrid, a DNA-protein complex or an RNA-protein complex.

A further aspect of the invention relates to an immunological composition that when introduced into an individual, preferably a human, capable of having induced within it an immunological response, induces an immunological response in such individual to a priA polynucleotide and/or polypeptide encoded therefrom, wherein the composition comprises a recombinant priA polynucleotide and/or polypeptide encoded therefrom and/or comprises DNA and/or RNA which encodes and expresses an antigen of said priA polynucleotide, polypeptide encoded therefrom, or other polypeptide of the invention. The immunological response may be used therapeutically or prophylactically and may take the form of antibody immunity and/or cellular immunity, such as cellular immunity arising from CTL or CD4+ T cells.

A priA polypeptide or a fragment thereof may be fused with co-protein or chemical moiety which may or may not by itself produce antibodies, but which is capable of stabilizing the first protein and producing a fused or modified protein which will have antigenic and/or immunogenic properties, and preferably protective properties. Thus fused recombinant protein, preferably further comprises an antigenic co-protein, such as lipoprotein D from *Hemophilus influenzae*, Glutathione-S-transferase (GST) or beta-galactosidase, or any other relatively large co-protein which solubilizes the protein and facilitates production and purification thereof. Moreover, the co-protein may act as an adjuvant in the sense of providing a generalized stimulation of the immune system of the organism receiving the protein. The co-protein may be attached to either the amino- or carboxy-terminus of the first protein.

Provided by this invention are compositions, particularly vaccine compositions, and methods comprising the polypeptides and/or polynucleotides of the invention and immunostimulatory DNA sequences, such as those described in Sato, Y. et al. *Science* 273: 352 (1996).

Also, provided by this invention are methods using the described polynucleotide or particular fragments thereof, which have been shown to encode non-variable regions of bacterial cell surface proteins, in polynucleotide constructs used in such genetic immunization experiments in animal models of infection with Streptococcus pneumoniae. Such experiments will be particularly useful for identifying protein epitopes able to provoke a prophylactic or therapeutic immune response. It is believed that this approach will allow for the subsequent preparation of monoclonal antibodies of particular value, derived from the requisite organ of the animal successfully resisting or clearing infection, for the development of prophylactic agents or therapeutic treatments of bacterial infection, particularly *Streptococcus pneumoniae* infection, in mammals, particularly humans.

A polypeptide of the invention may be used as an antigen for vaccination of a host to produce specific antibodies which protect against invasion of bacteria, for example by blocking adherence of bacteria to damaged tissue. Examples of tissue damage include wounds in skin or connective tissue caused, for example, by mechanical, chemical, thermal or radiation damage or by implantation of indwelling devices, or wounds in the mucous membranes, such as the mouth, throat, mammary glands, urethra or vagina.

The invention also includes a vaccine formulation which comprises an immunogenic recombinant polypeptide and/or polynucleotide of the invention together with a suitable carrier, such as a pharmaceutically acceptable carrier. Since the polypeptides and polynucleotides may be broken down in the stomach, each is preferably administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostatic compounds and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampoules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain priA polypeptides and polynucleotides, it is to be understood that this covers fragments of the naturally occurring polypeptides and polynucleotides, and similar polypeptides and polynucleotides with additions, deletions or substitutions which do not substantially affect the immunogenic properties of the recombinant polypeptides or polynucleotides.

Compositions, Kits and Administration

In a further aspect of the invention there are provided compositions comprising a priA polynucleotide and/or a priA polypeptide for administration to a cell or to a multicellular organism The invention also relates to compositions comprising a polynucleotide and/or a polypeptides discussed herein or their agonists or antagonists. The polypeptides and polynucleotides of the invention may be employed in combination with a non-sterile or sterile carrier or carriers for use with cells, tissues or organisms, such as a pharmaceutical carrier suitable for administration to an individual. Such compositions comprise, for instance, a media additive or a therapeutically effective amount of a polypeptide and/or polynucleotide of the invention and a pharmaceutically acceptable carrier or excipient. Such carriers may include, but are not limited to, saline, buffered saline, dextrose, water, glycerol, ethanol and combinations thereof. The formulation should suit the mode of administration. The invention further relates to diagnostic and pharmaceutical packs and kits comprising one or more containers filled with one or more of the ingredients of the aforementioned compositions of the invention.

Polypeptides, polynucleotides and other compounds of the invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes among others.

In therapy or as a prophylactic, the active agent may be administered to an individual as an injectable composition, for example as a sterile aqueous dispersion, preferably isotonic.

Alternatively the composition may be formulated for topical application for example in the form of ointments, creams, lotions, eye ointments, eye drops, ear drops, mouthwash, impregnated dressings and sutures and aerosols, and may contain appropriate conventional additives, including, for example, preservatives, solvents to assist drug penetration, and emollients in ointments and creams. Such topical formulations may also contain compatible conventional carriers, for example cream or ointment bases, and ethanol or oleyl alcohol for lotions. Such carriers may constitute from about 1% to about 98% by weight of the formulation; more usually they will constitute up to about 80% by weight of the formulation.

In a further aspect, the present invention provides for pharmaceutical compositions comprising a therapeutically effective amount of a polypeptide and/or polynucleotide, such as the soluble form of a polypeptide and/or polynucleotide of the present invention, agonist or antagonist peptide or small molecule compound, in combination with a pharmaceutically acceptable carrier or excipient. Such carriers include, but are not limited to, saline, buffered saline, dextrose, water, glycerol, ethanol, and combinations thereof. The invention further relates to pharmaceutical packs and kits comprising one or more containers filled with one or more of the ingredients of the aforementioned compositions of the invention. Polypeptides, polynucleotides and other compounds of the present invention may be employed alone or in conjunction with other compounds, such as therapeutic compounds.

The composition will be adapted to the route of administration, for instance by a systemic or an oral route. Preferred forms of systemic administration include injection, typically by intravenous injection. Other injection routes, such as subcutaneous, intramuscular, or intraperitoneal, can be used. Alternative means for systemic administration include transmucosal and transdernal administration using penetrants such as bile salts or fusidic acids or other detergents. In addition, if a polypeptide or other compounds of the present invention can be formulated in an enteric or an encapsulated formulation, oral administration may also be possible. Administration of these compounds may also be topical and/or localized, in the form of salves, pastes, gels, and the like.

For administration to mammals, and particularly humans, it is expected that the daily dosage level of the active agent will be from 0.01 mg/kg to 10 mg/kg, typically around 1 mg/kg. The physician in any event will determine the actual dosage which will be most suitable for an individual and will vary with the age, weight and response of the particular individual. The above dosages are exemplary of the average case. There can, of course, be individual instances where higher or lower dosage ranges are merited, and such are within the scope of this invention.

In-dwelling devices include surgical implants, prosthetic devices and catheters, i.e., devices that are introduced to the body of an individual and remain in position for an extended time. Such devices include, for example, artificial joints, heart valves, pacemakers, vascular grafts, vascular catheters, cerebrospinal fluid shunts, urinary catheters, continuous ambulatory peritoneal dialysis (CAPD) catheters.

The composition of the invention may be administered by injection to achieve a systemic effect against relevant bacteria shortly before insertion of an in-dwelling device. Treatment may be continued after surgery during the in-body time of the device. In addition, the composition could also be used to broaden perioperative cover for any surgical technique to prevent bacterial wound infections, especially *Streptococcus pneumoniae* wound infections.

Many orthopedic surgeons consider that humans with prosthetic joints should be considered for antibiotic prophylaxis before dental treatment that could produce a bacteremia. Late deep infection is a serious complication sometimes leading to loss of the prosthetic joint and is accompanied by significant morbidity and mortality. It may therefore be possible to extend the use of the active agent as a replacement for prophylactic antibiotics in this situation.

In addition to the therapy described above, the compositions of this invention may be used generally as a wound treatment agent to prevent adhesion of bacteria to matrix proteins exposed in wound tissue and for prophylactic use in dental treatment as an alternative to, or in conjunction with, antibiotic prophylaxis.

Alternatively, the composition of the invention may be used to bathe an indwelling device immediately before insertion. The active agent will preferably be present at a concentration of 1 μg/ml to 10 mg/ml for bathing of wounds or indwelling devices.

A vaccine composition is conveniently in injectable form. Conventional adjuvants may be employed to enhance the immune response. A suitable unit dose for vaccination is 0.5–5 microgram/kg of antigen, and such dose is preferably administered 1–3 times and with an interval of 1–3 weeks. With the indicated dose range, no adverse toxicological effects will be observed with the compounds of the invention which would preclude their administration to suitable individuals.

Sequence Databases, Sequences in a Tangible Medium, and Algorithms

Polynucleotide and polypeptide sequences form a valuable information resource with which to determine their 2- and 3-dimensional structures as well as to identify further sequences of similar homology. These approaches are most easily facilitated by storing the sequence in a computer readable medium and then using the stored data in a known macromolecular structure program or to search a sequence database using well known searching tools, such as GCC.

The polynucleotide and polypeptide sequences of the invention are particularly useful as components in databases useful for search analyses as well as in sequence analysis algorithms. As used in this section entitled "Sequence Databases, Sequences in a Tangible Medium, and Algorithmns," and in claims related to this section, the terms "polynucleotide of the invention" and "polynucleotide sequence of the invention" mean any detectable chemical or physical characteristic of a polynucleotide of the invention that is or may be reduced to or stored in a tangible medium, preferably a computer readable form. For example, chromatographic scan data or peak data, photographic data or scan data therefrom, called bases, and mass spectrographic data. As used in this section entitled Databases and Algorithms and in claims related thereto, the terms "polypeptide of the invention" and "polypeptide sequence of the invention" mean any detectable chemical or physical characteristic of a polypeptide of the invention that is or may be reduced to or stored in a tangible medium, preferably a computer readable form. For example, chromatographic scan data or peak data, photographic data or scan data therefrom, and mass spectrographic data.

The invention provides a computer readable medium having stored thereon polypeptide sequences of the invention and/or polynucleotide sequences of the invention. For example, a computer readable medium is provided comprising and having stored thereon a member selected from the group consisting of: a polynucleotide comprising the sequence of a polynucleotide of the invention; a polypeptide comprising the sequence of a polypeptide sequence of the invention; a set of polynucleotide sequences wherein at least one of the sequences comprises the sequence of a polynucleotide sequence of the invention; a set of polypeptide sequences wherein at least one of the sequences comprises the sequence of a polypeptide sequence of the invention; a data set representing a polynucleotide sequence comprising the sequence of polynucleotide sequence of the invention; a data set representing a polynucleotide sequence encoding a polypeptide sequence comprising the sequence of a polypeptide sequence of the invention; a polynucleotide comprising the sequence of a polynucleotide sequence of the invention; a polypeptide comprising the sequence of a polypeptide sequence of the invention; a set of polynucleotide sequences wherein at least one of the sequences comprises the sequence of a polynucleotide sequence of the invention; a set of polypeptide sequences wherein at least one of said sequences comprises the sequence of a polypeptide sequence of the invention; a data set representing a polynucleotide sequence comprising the sequence of a polynucleotide sequence of the invention; a data set representing a polynucleotide sequence encoding a polypeptide sequence comprising the sequence of a polypeptide sequence of the invention. The computer readable medium can be any composition of matter used to store information or data, including, for example, commercially available floppy disks, tapes, chips, hard drives, compact disks, and video disks.

Also provided by the invention are methods for the analysis of character sequences or strings, particularly genetic sequences or encoded genetic sequences. Preferred methods of sequence analysis include, for example, methods of sequence homology analysis, such as identity and similarity analysis, RNA structure analysis, sequence assembly, cladistic analysis, sequence motif analysis, open reading frame determination, nucleic acid base calling, nucleic acid base trimming, and sequencing chromatogram peak analysis.

A computer based method is provided for performing homology identification. This method comprises the steps of providing a polynucleotide sequence comprising the sequence a polynucleotide of the invention in a computer readable medium; and comparing said polynucleotide sequence to at least one polynucleotide or polypeptide sequence to identify homology.

A computer based method is also provided for performing homology identification, said method comprising the steps of: providing a polypeptide sequence comprising the sequence of a polypeptide of the invention in a computer readable medium; and comparing said polypeptide sequence to at least one polynucleotide or polypeptide sequence to identify homology.

A computer based method is still further provided for polynucleotide assembly, said method comprising the steps of: providing a first polynucleotide sequence comprising the sequence of a polynucleotide of the invention in a computer readable medium; and screening for at least one overlapping region between said first polynucleotide sequence and a second polynucleotide sequence.

A further embodiment of the invention provides a computer based method for performing homology identification, said method comprising the steps of: providing a polynucleotide sequence comprising the sequence of a polynucleotide of the invention in a computer readable medium; and comparing said polynucleotide sequence to at least one polynucleotide or polypeptide sequence to identify homology.

A further embodiment of the invention provides a computer based method for performing homology identification, said method comprising the steps of: providing a polypeptide sequence comprising the sequence of a polypeptide of the invention in a computer readable medium; and comparing said polypeptide sequence to at least one polynucleotide or polypeptide sequence to identify homology.

A further embodiment of the invention provides a computer based method for polynucleotide assembly, said method comprising the steps of: providing a first polynucleotide sequence comprising the sequence of a polynucleotide of the invention in a computer readable medium; and screening for at least one overlapping region between said first polynucleotide sequence and a second polynucleotide sequence.

In another preferred embodiment of the invention there is provided a computer readable medium having stored thereon a member selected from the group consisting of: a polynucleotide comprising the sequence of SEQ ID NO. 1; a polypeptide comprising the sequence of SEQ ID NO. 2; a set of polynucleotide sequences wherein at least one of said sequences comprises the sequence of SEQ ID NO. 1; a set of polypeptide sequences wherein at least one of said sequences comprises the sequence of SEQ ID NO. 2; a data set representing a polynucleotide sequence comprising the sequence of SEQ ID NO. 1; a data set representing a polynucleotide sequence encoding a polypeptide sequence comprising the sequence of SEQ ID NO.2; a polynucleotide comprising the sequence of SEQ ID NO. 1; a polypeptide comprising the sequence of SEQ ID NO. 2; a set of polynucleotide sequences wherein at least one of said sequences comprises the sequence of SEQ ID NO. 1, a set of polypeptide sequences wherein at least one of said sequences comprises the sequence of SEQ ID NO. 2; a data set representing a polynucleotide sequence comprising the sequence of SEQ ID NO. 1; a data set representing a polynucleotide sequence encoding a polypeptide sequence comprising the sequence of SEQ ID NO. 2. A further preferred embodiment of the invention provides a computer based method for performing homology identification, said method comprising the steps of providing a polynucleotide sequence comprising the sequence of SEQ ID NO. 1 in a computer readable medium; and comparing said polynucleotide sequence to at least one polynucleotide or polypeptide sequence to identify homology.

A still further preferred embodiment of the invention provides a computer based method for performing homology identification, said method comprising the steps of: providing a polypeptide sequence comprising the sequence of SEQ ID NO. 2 in a computer readable medium; and comparing said polypeptide sequence to at least one polynucleotide or polypeptide sequence to identify homology.

A further embodiment of the invention provides a computer based method for polynucleotide assembly, said method comprising the steps of: providing a first polynucleotide sequence comprising the sequence of SEQ ID NO.1 in a computer readable medium; and screening for at least one overlapping region between said first polynucleotide sequence and a second polynucleotide sequence.

A further embodiment of the invention provides a computer based method for performing homology identification, said method comprising the steps of: providing a polynucleotide sequence comprising the sequence of SEQ ID NO. 1 in a computer readable medium; and comparing said polynucleotide sequence to at least one polynucleotide or polypeptide sequence to identify homology.

A further embodiment of the invention provides a computer based method for performing homology identification, said method comprising the steps of providing a polypeptide sequence comprising the sequence of SEQ ID NO. 2 in a computer readable medium; and comparing said polypeptide sequence to at least one polynucleotide or polypeptide sequence to identify homology.

A further embodiment of the invention provides a computer based method for polynucleotide assembly, said method comprising the steps of: providing a first polynucleotide sequence comprising the sequence of SEQ ID NO. 1 in a computer readable medium; and screening for at least one overlapping region between said first polynucleotide sequence and a second polynucleotide sequence.

All publications and references, including but not limited to patents and patent applications, cited in this specification are herein incorporated by reference in their entirety as if each individual publication or reference were specifically and individually indicated to be incorporated by reference herein as being fully set forth. Any patent application to which this application claims priority is also incorporated by reference herein in its entirety in the manner described above for publications and references.

Glossary

The following definitions are provided to facilitate understanding of certain terms used frequently herein.

"Antibody(ies)" as used herein includes polyclonal and monoclonal antibodies, chimeric, single chain, and humanized antibodies, as well as Fab fragments, including the products of an Fab or other immunoglobulin expression library.

"Antigenically equivalent derivative(s)" as used herein encompasses a polypeptide, polynucleotide, or the equivalent of either which will be specifically recognized by certain antibodies which, when raised to the protein, polypeptide or polynucleotide according to the invention, interferes with the immediate physical interaction between pathogen and mammalian host.

"Bispecific antibody(ies)" means an antibody comprising at least two antigen binding domains, each domain directed against a different epitope.

"Bodily material(s)" means any material derived from an individual or from an organism infecting, infesting or inhabiting an individual, including but not limited to, cells, tissues and waste, such as, bone, blood, serum, cerebrospinal fluid, semen, saliva, muscle, cartilage, organ tissue, skin, urine, stool or autopsy materials.

"Disease(s)" means any disease caused by or related to infection by a bacteria, including, for example, otitis media, conjunctivitis, pneumonia, bacteremia, meningitis, sinusitis, pleural empyema and endocarditis, and most particularly meningitis, such as for example infection of cerebrospinal fluid.

"Fusion protein(s)" refers to a protein encoded by two, often unrelated, fused genes or fragments thereof. In one example, EP-A-0464 discloses fusion proteins comprising various portions of constant region of immunoglobulin molecules together with another human protein or part thereof. In many cases, employing an immunoglobulin Fc region as a part of a fusion protein is advantageous for use in therapy and diagnosis resulting in, for example, improved pharmacokinetic properties [see, e.g., EP-A 02322621]. On the other hand, for some uses it would be desirable to be able to delete the Fc part after the fusion protein has been expressed, detected and purified.

"Host cell(s)" is a cell which has been transformed or transfected, or is capable of transformation or transfection by an exogenous polynucleotide sequence.

"Identity," as known in the art, is a relationship between two or more polypeptide sequences or two or more polynucleotide sequences, as the case maybe, as determined by comparing the sequences. In the art, "identity" also means the degree of sequence relatedness between polypeptide or polynucleotide sequences, as the case may be, as determined by the match between strings of such sequences. "Identity" can be readily calculated by known methods, including but not limited to those described in (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part I, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991; and Carillo, H., and Lipman, D., SIAM *J. Applied Math.*, 48: 1073 (1988). Methods to determine identity are designed to give the largest match between the sequences tested. Moreover, methods to determine identity are codified in publicly available computer programs. Computer program methods to determine identity between two sequences include, but are not limited to, the GCG program package (Devereux, J., et al., *Nucleic Acids Research* 12(1): 387 (1984)), BLASTP, BLASTN, and FASTA (Altschul, S. F. et al., *J. Molec. Biol.* 215: 403–410 (1990). The BLAST X program is publicly available from NCBI and other sources (*BLAST Manual*, Altschul, S., et al., NCBI NLM NIH Bethesda, Md. 20894; Altschul, S., et al., *J. Mol. Biol.* 215: 403–410 (1990). The well known Smith Waterman algorithm may also be used to determine identity.

Parameters for polypeptide sequence comparison include the following:

1) Algorithm: Needleman and Wunsch, J. Mol Biol. 48: 443–453 (1970)

Comparison matrix: BLOSSUM62 from Hentikoff and Hentikoff, Proc. Natl. Acad. Sci. U.S.A. 10 89:10915–10919 (1992)

Gap Penalty: 12

Gap Length Penalty: 4

A program useful with these parameters is publicly available as the "gap" program from Genetics Computer Group, Madison Wis. The aforementioned parameters are the default parameters for peptide comparisons (along with no penalty for end gaps).

Parameters for polynucleotide comparison include the following:

1) Algorithm: Needleman and Wunsch, J. Mol Biol. 48: 443–453 (1970)
Comparison matrix: matches=+10, mismatch=0
Gap Penalty: 50
Gap Length Penalty: 3
Available as: The "gap" program from Genetics Computer Group, Madison Wis. These are the default parameters for nucleic acid comparisons.

A preferred meaning for "identity" for polynucleotides and polypeptides, as the case may be, are provided in (1) and (2) below.

(1) Polynucleotide embodiments further include an isolated polynucleotide comprising a polynucleotide sequence having at least a 50, 60, 70, 80, 85, 90, 95, 97 or 100% identity to the reference sequence of SEQ ID NOs:1 or 5, wherein said polynucleotide sequence may be identical to the reference sequence of SEQ ID NO: 1 or may include up to a certain integer number of nucleotide alterations as compared to the reference sequence, wherein said alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence, and wherein said number of nucleotide alterations is determined by multiplying the total number of nucleotides in SEQ ID NOs:1 or 5 by the integer defining the percent identity divided by 100 and then subtracting that product from said total number of nucleotides in SEQ ID NOs:1 or 5, or:

$$n_n \leq x_n - (x_n \cdot y),$$

wherein $n_n$ is the number of nucleotide alterations, $x_n$ is the total number of nucleotides in SEQ ID NOs:1 or 5, y is 0.50 for 50%, 0.60 for 60%, 0.70 for 70%, 0.80 for 80%, 0.85 for 0.90 for 90%, 0.95 for 95%, 0.97 for 97% or 1.00 for 100%, and · is the symbol for the multiplication operator, and wherein any non-integer product of $x_n$ and y is rounded down to the nearest integer prior to subtracting it from $x_n$. Alterations of a polynucleotide sequence encoding the polypeptide of SEQ ID NO:2 may create nonsense, missense or frameshift mutations in this coding sequence and thereby alter the polypeptide encoded by the polynucleotide following such alterations.

By way of example, a polynucleotide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one nucleic acid deletion, substitution, including transition and transversion, or insertion, and wherein said alterations may occur at the 5' or 3' terminal positions of the reference polynucleotide sequence or anywhere between those terminal positions, interspersed either individually among the nucleic acids in the reference sequence or in one or more contiguous groups within the reference sequence. The number of nucleic acid alterations for a given percent identity is determined by multiplying the total number of amino acids in SEQ ID NO:2 by the integer defining the percent identity divided by 100 and then subtracting that product from said total number of amino acids in SEQ ID NO:2, or:

$$n_n \leq x_n - (x_n \cdot y),$$

wherein $n_n$ is the number of amino acid alterations, $x_n$ is the total number of amino acids in SEQ ID NO:2, y is, for instance 0.70 for 70%, 0.80 for 80%, 0.85 for 85% etc., · is the symbol for the multiplication operator, and wherein any non-integer product of $x_n$ and y is rounded down to the nearest integer prior to subtracting it from $x_n$.

(2) Polypeptide embodiments further include an isolated polypeptide comprising a polypeptide having at least a 50, 60, 70, 80, 85, 90, 95, 97 or 100% identity to a polypeptide reference sequence of SEQ ID NO:2, wherein said polypeptide sequence may be identical to the reference sequence of SEQ ID NO: 2 or may include up to a certain integer number of amino acid alterations as compared to the reference sequence, wherein said alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence, and wherein said number of amino acid alterations is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is 0.50 for 50%, 0.60 for 60%, 0.70 for 70%, 0.80 for 80%, 0.85%, for 0.90 for 90%, 0.95 for 95%, 0.97 for 97% or 1.00 for 100%, and · is the symbol for the multiplication operator, and wherein any non-integer product of $x_a$ and y is rounded down to the nearest integer prior to subtracting it from $x_a$.

By way of example, a polypeptide sequence of the present invention may be identical to the reference sequence of SEQ ID NO:2, that is it may be 100% identical, or it may include up to a certain integer number of amino acid alterations as compared to the reference sequence such that the percent identity is less than 100% identity. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in SEQ ID NO:2 by the integer defining the percent identity divided by 100 and then subtracting that product from said total number of amino acids in SEQ ID NO:2, or:

$$n_a \leq x_a - (x_a \cdot y),$$

wherein $n_a$ is the number of amino acid alterations, $x_a$ is the total number of amino acids in SEQ ID NO:2, y is, for instance 0.70 for 70%, 0.80 for 80%, 0.85 for 85% etc., and · is the symbol for the multiplication operator, and wherein any non-integer product of $x_a$ and y is rounded down to the nearest integer prior to subtracting it from $x_a$.

"Immunologically equivalent derivative(s)" as used herein encompasses a polypeptide, polynucleotide, or the equivalent of either which when used in a suitable formulation to raise antibodies in a vertebrate, the antibodies act to interfere with the immediate physical interaction between pathogen and mammalian host.

"Immunospecific" means that characteristic of an antibody whereby it possesses substantially greater affinity for the polypeptides of the invention or the polynucleotides of the invention than its affinity for other related polypeptides or polynucleotides respectively, particularly those polypeptides and polynucleotides in the prior art.

"Individual(s)" means a multicellular eukaryote, including, but not limited to a metazoan, a mammal, an ovid, a bovid, a simian a primate, and a human.

"Isolated" means altered "by the hand of man" from its natural state, i.e., if it occurs in nature, it has been changed or removed from its original environment, or both. For example, a polynucleotide or a polypeptide naturally present in a living organism is not "isolated," but the same polynucleotide or polypeptide separated from the coexisting materials of its natural state is "isolated", as the term is employed herein. Moreover, a polynucleotide or polypeptide that is introduced into an organism by transformation, genetic manipulation or by any other recombinant method is "isolated" even if it is still present in said organism, which organism may be living or non-living.

"Organism(s)" means a (i) prokaryote, including but not limited to, a member of the genus Streptococcus, Staphylococcus, Bordetella, Corynebacterium, Mycobacterium, Neisseria, Haemophilus, Actinomycetes, Streptomycetes, Nocardia, Enterobacter, Yersinia, Fancisella, Pasturella, Moroxella, Acinetobacter, Erysipelothrix, Branhamella, Actinobacillus, Streptobacillus, Listeria, Calymmatobacterium, Brucella, Bacillus, Clostridium, Treponema, Escherichia, Salmonella, Kleibsiella, Vibrio, Proteus, Erwinia, Borrelia, Leptospira, Spirillum, Campylobacter, Sigella, Legionella, Pseudomonas, Aeromonas, Rickettsia, Chlamydia, Borrelia and Mycoplasma, and further including, but not limited to, a member of the species or group, Group A Streptococcus, Group B Streptococcus, Group C Streptococcus, Group D Streptococcus, Group G Streptococcus, *Streptococcus pneumoniae, Streptococcus pyogenes, Streptococcus agalactiae, Streptococcus faecalis, Streptococcus faecium, Streptococcus durans, Neisseria gonorrheae, Neisseria meningitides, Staphylococcus aureus, Staphylococcus epidermidis, Corynebacterium diptheriae, Gardnerella vaginalis, Mycobacterium tuberculosis, Mycobacterium bovis, Mycobacterium ulcerans, Mycobacterium leprae, Actinomyctes israelii, Listeria monocytogenes, Bordetella pertusis, Bordatella parapertusis, Bordetella bronchiseptica, Escherichia coli, Shigella dysenteriae, Haemophilus influenzae, Haemophilus aegyptius, Haemophilus parainfluenzae, Haemophilus ducreyl,* Bordetella, *Salmonella typhi, Citrobacter freundii, Proteus mirabilis, Proteus vulgaris, Yersinia pestis, Kleibsiella pneumoniae, Serratia marcessens, Serratia liquefaciens, Vibrio cholera, Shigella dysenterii, Shigella flexneri, Pseudomonas aeruginosa, Franscisella tularensis, Brucella abortis, Bacillus anthracis, Bacillus cereus, Clostridium perfringens, Clostridium tetani, Clostridium botulinum, Treponema pallidum, Rickettsia rickettsia* and *Chlamydia trachomitis,* (ii) an archaeon, including but not limited to Archaebacter, and (iii) a unicellular or filamentous eukaryote, including but not limited to, a protozoan, a fungus, a member of the genus Saccharomyces, Kluveromyces, or Candida, and a member of the species *Saccharomyces ceriviseae, Kluveromyces lactis,* or *Candida albicans.*

"Polynucleotide(s)" generally refers to any polyribonucleotide or polydeoxyribonucleotide, which may be unmodified RNA or DNA or modified RNA or DNA. "Polynucleotide(s)" include, without limitation, single- and double-stranded DNA, DNA that is a mixture of single- and double-stranded regions or single, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term "polynucleotide(s)" as it is employed herein embraces such chemically, enzymatically or metabolically modified forms of polynucleotides, as well as the chemical forms of DNA and RNA characteristic of viruses and cells, including, for example, simple and complex cells. "Polynucleotide(s)" also embraces short polynucleotides often referred to as oligonucleotide(s).

"Polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature, and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cysteine, formation of pyroglutamate, formylation, gammacarboxylation, GPI anchor formation, hydroxylation, iodination, methylation, myristoylation, oxidation, proteolytic processing, phosphorylation, prenylation, racemization, glycosylation, lipid attachment, sulfation, gammacarboxylation of glutamic acid residues, hydroxylation and ADP-ribosylation, selenoylation, sulfation, transfer-RNA mediated addition of amino acids to proteins, such as arginylation, and ubiquitination. See, for instance, PROTEINS—STRUCTURE AND MOLECULAR PROPERTIES, 2nd Ed., T. E. Creighton, W. H. Freeman and Company, New York (1993) and Wold, F., Posttranslational Protein Modifications: Perspectives and Prospects, pgs. 1–12 in POSTTRANSLATIONAL COVALENT MODIFICATION OF PROTEINS, B. C. Johnson, Ed., Academic Press, New York (1983); Seifter et al., Meth. Enzymol. 182:626–646 (1990) and Rattan et al., Protein Synthesis: Posttranslational Modifications and Aging, Ann. N.Y. Acad. Sci. 663: 48–62 (1992). Polypeptides may be branched or cyclic, with or without branching. Cyclic, branched and branched circular polypeptides may result from post-translational natural processes and may be made by entirely synthetic methods, as well.

"Recombinant expression system(s)" refers to expression systems or portions thereof or polynucleotides of the invention introduced or transformed into a host cell or host cell lysate for the production of the polynucleotides and polypeptides of the invention.

"Subtraction set" is one or more, but preferably less than 100, polynucleotides comprising at least one polynucleotide of the invention "Variant(s)" as the term is used herein, is a polynucleotide or polypeptide that differs from a reference polynucleotide or polypeptide respectively, but retains essential properties. A typical variant of a polynucleotide differs in nucleotide sequence from another, reference polynucleotide. Changes in the nucleotide sequence of the variant may or may not alter the amino acid sequence of a polypeptide encoded by the reference polynucleotide. Nucleotide changes may result in amino acid substitutions, additions, deletions, fusion proteins and truncations in the polypeptide encoded by the reference sequence, as discussed below. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more substitutions, additions, deletions in any combination. A substituted or inserted amino acid residue may or may not be one encoded by the genetic code. The present invention also includes include variants of each of the polypeptides of the invention, that is polypeptides that vary from the referents by conservative amino acid substitutions, whereby a residue is substituted by another with like characteristics. Typical such substitutions are among Ala, Val, Leu and Ile; among Ser and Thr; among the acidic residues Asp and Glu; among Asn and Gln; and among the basic residues Lys and Arg; or aromatic residues Phe and Tyr. Particularly preferred are variants in which several, 5–10, 1–5, 1–3, 1–2 or 1 amino acids are substituted, deleted, or added in any combination. A variant of a polynucleotide or polypeptide may be a naturally occurring such as an allelic variant, or it may be a variant that is not known to occur naturally. Non-naturally occurring variants of polynucleotides and polypeptides may be made by mutagenesis techniques, by direct synthesis, and by other recombinant methods known to skilled artisans.

EXAMPLES

The examples below are carried out using standard techniques, which are well known and routine to those of skill in the art, except where otherwise described in detail. The examples are illustrative, but do not limit the invention.

Example 1

Strain Selection, Library Production and Sequencing

The polynucleotide having a DNA sequence given in Table 1 [SEQ ID NOs:1 or 5] was obtained from a library of clones of chromosomal DNA of Streptococcus pneumoniae in E. coli. The sequencing data from two or more clones containing overlapping Streptococcus pneumoniae DNAs was used to construct the contiguous DNA sequence in SEQ ID NOs:1 or 5. Libraries may be prepared by routine methods, for example:
Methods 1 and 2 Below.

Total cellular DNA is isolated from Streptococcus pneumoniae 0100993 according to standard procedures and size-fractionated by either of two methods.

Method 1

Total cellular DNA is mechanically sheared by passage through a needle in order to size-fractionate according to standard procedures. DNA fragments of up to 11 kbp in size are rendered blunt by treatment with exonuclease and DNA polymerase, and EcoRI linkers added. Fragments are ligated into the vector Lambda ZapII that has been cut with EcoRI, the library packaged by standard procedures and E. coli infected with the packaged library. The library is amplified by standard procedures.

Method 2

Total cellular DNA is partially hydrolyzed with a one or a combination of restriction enzymes appropriate to generate a series of fragments for cloning into library vectors (e.g., RsaI, PalI, AluI, Bshl235I), and such fragments are size-fractionated according to standard procedures. EcoRI linkers are ligated to the DNA and the fragments then ligated into the vector Lambda ZapII that have been cut with EcoRI, the library packaged by standard procedures, and E. coli infected with the packaged library. The library is amplified by standard procedures.

Example 2 priA Characterization

Replication of the lagging strand of DNA is mediated by a multiprotein complex composed of proteins n , priA, n", dnaT, dnaB, dnaC, and dnaG. This complex is referred to as a primosome. Purified priA has ATPase, helicase, translocase, and primosome assembly activities (Lee E H, Masai H, Allen G C Jr, Kornberg A, Proc Natl Acad Sci U.S.A. 1990 June, 87 (12): 4620–4624) (Sandler S J, Samra H S, Clark A J Genetics 1996 May;143(1):5–13). This gene may be essential in recombination and DNA repair since it binds to D-loops, interacts with recG and has helicase activity (McGlynn P, Al-Deib A A, Liu J, Marians K J, Lloyd R G J Mol Biol 1997 July 11;270(2):212–221). The 3'-5' DNAhelicase activity of priA inhibits recombination (Al-Deib A A, Mahdi A A, Lloyd R G Bacteriol 1996 December;178(23):6782–6789). Insertion mutants of priA are Rec- and UVS which is a flmction of its primosome assembly function (Sandler S J, Samra H S, Clark A J Genetics 1996 May;143(l):5–13). Null mutants of priA are also defective in transductional and conjugational recombination (Kogoma T, Cadwell G W, Barnard K G, Asai T J Bacteriol 1996 March;178(5):1258–1264). Null mutants can be suppressed by mutations mapping to dnaC.

What is claimed is:

1. An isolated polynucleotide comprising a first polynucleotide or the full complement of the entire length of the first polynucleotide, wherein the first polynucleotide encodes a polypeptide comprising the amino acid sequence set forth in SEQ ID NO:2.

2. The isolated polynucleotide of claim 1, wherein the isolated polynucleotide comprises the first polynucleotide.

3. A vector comprising the isolated polynucleotide of claim 2.

4. An isolated host cell comprising the vector of claim 3.

5. A process for producing a polypeptide comprising the step of culturing the host cell of claim 4 under conditions sufficient for the production of the polypeptide, wherein the polypeptide is encoded by the first polynucleotide.

6. The isolated polynucleotide of claim 1, wherein the isolated polynucleotide comprises the full complement of the entire length of the first polynucleotide.

7. A vector comprising the isolated polynucleotide of claim 6.

8. An isolated host cell comprising the vector of claim 7.

9. The isolated polynucleotide of claim 2 encoding a fusion polypeptide, wherein the first polynucleotide encodes part of the fusion polypeptide.

10. An isolated polynucleotide comprising a first polynucleotide or the full complement of the entire length of the first polynucleotide, wherein the first polynucleotide comprises SEQ ID NO:1.

11. The isolated polynucleotide of claim 10, wherein the isolated polynucleotide comprises the first polynucleotide.

12. A vector comprising the isolated polynucleotide of claim 11.

13. An isolated host cell comprising the vector of claim 12.

14. A process for producing a polypeptide comprising the step of culturing the host cell of claim 13 under conditions sufficient for the production of the polypeptide, wherein the polypeptide is encoded by the first polynucleotide.

15. The isolated polynucleotide of claim 10, wherein the isolated polynucleotide comprises the full complement of the entire length of the first polynucleotide.

16. A vector comprising the isolated polynucleotide of claim 15.

17. An isolated host cell comprising the vector of claim 16.

18. The isolated polynucleotide of claim 10 encoding a fusion polypeptide, wherein the first polynucleotide encodes part of the fusion polypeptide.

19. An isolated polynucleotide comprising a first polynucleotide or the full complement of the entire length of the first polynucleotide, wherein the first polynucleotide encodes a polypeptide consisting of the amino acid sequence set forth in SEQ ID NO.2.

20. The isolated polynucleotide of claim 19, wherein the isolated polynucleotide comprises the first polynucleotide.

21. A vector comprising the isolated polynucleotide of claim 20.

22. An isolated host cell comprising the vector of claim 21.

23. A process for producing a polypeptide comprising the step of culturing the host cell of claim 22 under conditions sufficient for the production of the polypeptide, wherein the polypeptide is encoded by the first polynucleotide.

24. The isolated polynucleotide of claim 19, wherein the isolated polynucleotide comprises the full complement of the entire length of the first polynucleotide.

25. A vector comprising the isolated polynucleotide of claim 24.

26. An isolated host cell comprising the vector of claim 25.

* * * * *

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 3015 base pairs
        (B) TYPE: nucleic acid
        (C) STRANDEDNESS: double
        (D) TOPOLOGY: linear (xi) SEQUENCE DESCRIPTION: SEQ ID NO:1:

```
TTCGATTTGC TGAAACGTGT CAAATGTGTG ATTGAAGCAG AACACTTCTG TGTGGATCGT      60

GTCATTGGTC ACTATCAGGA GATGTTACCA AAATCTCCAA CTACCCGATA AAATTTAGAA     120

AATAGGTACA AGCAAATGAT GTTAAAACCC TCTATTGATA CCTTGCTCGA CAAGGTTCCT     180

TCAAAATATT CACTCGTAAT CTTGGAAGCA AAACGTGCCC ACGAATTGGA AGCAGGTGCC     240

CCAGCAACTC AAGGTTTCAA GTCTGAAAAA TCAACTCTTC GCGCTTTAGA AGAAATCGAA     300

TCAGGAAACG TTACAATTCA CCCAGATCCA GAAGGAAAAC GTGAAGCAGT GCGTCGCCGT     360

ATCGAAGAAG AAAAACGCCG CAAAGAAGAA GAAGAAAAGA AAATCAAAGA GCAAATTGCT     420

AAAGAAAAAG AAGATGGTGA AAAAATTTAA GGTTGGGGGG ACTCAATCTT ATTTTTTCTA     480

TTGCAAGAAT GTACTGACAA GGAGGAGGTG AGAAGATGGC CCTAGCTAAG ATTATCGTAG     540

ATGTGCCCTT GATGCAGACG GACCAGCCCT ATAGTTACAG GATTCCGGAG GAATTTGAGG     600

GAATGCTGGA AGTTGGGATG CGGGTTCATG TGCCTTTTGG TAAGGGTAAT CGCCTGATTC     660

AAGGGATTGT TCTTGGTTTG GAGTCCCAAT CAGATGGAGA AGAGATGGAG CAAGATTTAA     720

AAGATATTGC AGAGGTGCTG GATTTTTCTC CTGTTCTCAC GCCAGAACAA CTCTGGCTGG     780

CTGAGGAGTT ACGCAAATCT GTCTTCTCCT ACAAAATTTC TATCCTCAAG GCCATGCTTC     840

CAGGATTTCT GAATTCTAGC TATGACAAGA TTCTCTATCC TCTGGAAGGC TTGAGTCAGG     900

AAGAACGAGT GCGCCTGTTT GGTTCAGAAG ATTCGCTAGC CTTTTCTTCA CTAGACCTTG     960

CCAAGCAAGC TGAAATGATG CGTTTGACTA GAAAAGGCCT GCTTGGTCTG AATATCAGG     1020

CAGTCGATCA AAAGAAGGTC AAGACCCAGT CTTGGTATGA GGTTGACCAT GCTCAATTAG    1080

AAGGTGTTGA GATTTCTACA CGTGCCAAGA AAAAGTTGGA ACTGAGAGAT TATCTGCTGT    1140

CTCATCCAGA GAGCGCTTCC TTGGCTAGCT TGTTAGAGTC CTACTCGCGA GAGCAAGTCA    1200

ACTTCTTTGT GGATCAAGGT GCTGTTACCA TAGTCCAAAA GGAAGTTCAA CGCTCGGCTG    1260

CTTATTTTGA AGGAATTGAA GCAAGTAGAC CTTTGGAGTT AAATCCAGAA CAAAGACAGG    1320

CGCGTGATGC GGTTGTGAGT TCTATTGGCA GTTCTCAACC TCCCTTTCTA CTTCAAGGGA    1380

TTACAGGAAG TGGGAAGACC GAGGTTTACT TGCAGATTAT CCAAGGTGCC CTGGATAAGG    1440

GCAAGACAGC TATTTTGCTG GTACCTGAGA TTTCCTTGAC TCCTCAGATG ACCGAGCGTT    1500

TTATAGCACG TTTTGGGGAC AAGGTAGCCA TTCTTCACTC AGGATTATCC AATGGTGAAA    1560

AGTATGATGA ATGGCGCAAG GTGGAGCGTG GCGATGCCCA AGTTGTTGTT GGTGCCAGAT    1620

CTGCTATCTT TGCTCCTCTG AAAAATCTGG GTGTCATGAT TATTGATGAA GAGCATGAAG    1680

CGGCTTATAA GCAGGACAGC AATCCCCGTT ACCATGCCAG AGAGGTAGCT ATTTTACGGG    1740

CTCAGTATAA TCAAGCAACT CTGGTACTTG GATCTGCAAC GCCGAGCTTA GAGAGCCGGG    1800

CACGTGCTGG CAAAGGCGTC TATCAACACT TACGTCTAAC CCAACGTGCC AATCCTTTGG    1860
```

```
CTACAATCCC TGAGGTTCAA GTGATTGACT TTCGAGACTA TATCGGACAA AATGAGACGT    1920

CAAACTTTAC GCCTCCTTTG CTAGAGGCTA TCCAAGACCG TCTGGTTAAA AAAGAGCAGA    1980

TGGTTCTCAT GCTCAATCGC CGTGGTTATT CTAGCTTTGT CATGTGTCGG GAGTGTGGGA    2040

CGGTGGATAC TTGTCCCAAC TGTGATATTT CTCTGACCTT GCATATGGAT ACCAAGACTA    2100

TGAACTGCCA TTATTGTGGT TTCTCGAAGG ATATTCCTCA GGTCTGTCCT AACTGTAAGA    2160

GCCACAGTAT TCGTTACTAT GGGACGGGAA CTCAGAAGGC TTATGATGAG CTAGCAGAAC    2220

TCTTTCCCCA AGCTCGCATT TGAGGATGG ATGTGGATAC GACTCGAAAG AAAGGCAGTC     2280

ACCAAGCCTT GCTTGACCAG TTTGGGCGAG GGGAAGCGGA TATTTTACTT GGTACTCAGA    2340

TGATTGCAAA GGGTTTGGAT TTTCCCAATG TTACCCTAGT CGGAGTTCTA AATGCGGATA    2400

CGGCCTTGAA TCTGCCTGAT TTCCGTTCTT CTGAGAGAAC CTTCCAGCTC TTGACTCAGG    2460

TGGCAGGTCG AGCAGGTCGT GCTGAAAAGG CAGGTCAAGT CTTGATACAG TCCTACAATC    2520

CGCAGCACTA TGCTATTCGA TTTGCCAAGG ATCAAGATTA CGAAGGCTTT TATGCCTATG    2580

AAATGGGAAT CAGACGACAA CTCGGCTATC CACCTTACTA TTTCACGATT GGTATTACCC    2640

TTTCTCACAA GAAAGAAGAA GAGGTTTTCA AACGTGCCTA TGAAGTCATG AACATTTTGC    2700

GGTCAGGCTT GTCAGAGACC AGTCCCATTC TGGGGCCAAC GCCAAAACCG ATTGCCCGTA    2760

CCCACAACCT CTATCATTAC CAGATTTTAA TTAAATACCG TTTAGAAGAT GAGCTGGGGC    2820

CGACCCTCAA CCAGGTCCTG GCCTTGACTC AAGAACGGGA AAATAGTGAG CTCCGTCTCA    2880

GCATTGACCA TGAGCCGCAG CAATTTTTAT AAGAAGGAGA AGATATGACA AAACTAATCT    2940

TTATGGGGAC CCCCGACTTT TCAGCAACAG TCTTAAAAGG ACTTTTGACA GATGACCGTT    3000

ACGAAATTCT AGCCG                                                    3015

(2) INFORMATION FOR SEQ ID NO:2:

(i) SEQUENCE CHARACTERISTICS:
        (A) LENGTH: 804 amino acids
        (B) TYPE: amino acid
        (C) STRANDEDNESS: single
        (D) TOPOLOGY: linear (xi) SEQUENCE DESCRIPTION: SEQ ID NO:2:

Gln Gly Gly Gly Glu Lys Met Ala Leu Ala Lys Ile Ile Val Asp Val
1               5                   10                  15

Pro Leu Met Gln Thr Asp Gln Pro Tyr Ser Tyr Arg Ile Pro Glu Glu
            20                  25                  30

Phe Glu Gly Met Leu Glu Val Gly Met Arg Val His Val Pro Phe Gly
        35                  40                  45

Lys Gly Asn Arg Leu Ile Gln Gly Ile Val Leu Gly Leu Glu Ser Gln
    50                  55                  60

Ser Asp Gly Glu Glu Met Glu Gln Asp Leu Lys Asp Ile Ala Glu Val
65                  70                  75                  80

Leu Asp Phe Ser Pro Val Leu Thr Pro Glu Gln Leu Trp Leu Ala Glu
                85                  90                  95

Glu Leu Arg Lys Ser Val Phe Ser Tyr Lys Ile Ser Ile Leu Lys Ala
            100                 105                 110

Met Leu Pro Gly Phe Leu Asn Ser Ser Tyr Asp Lys Ile Leu Tyr Pro
        115                 120                 125

Leu Glu Gly Leu Ser Gln Glu Glu Arg Val Arg Leu Phe Gly Ser Glu
    130                 135                 140
```

-continued

```
Asp Ser Leu Ala Phe Ser Ser Leu Asp Leu Ala Lys Gln Ala Glu Met
145                 150                 155                 160

Met Arg Leu Thr Arg Lys Gly Leu Leu Gly Leu Glu Tyr Gln Ala Val
            165                 170                 175

Asp Gln Lys Lys Val Lys Thr Gln Ser Trp Tyr Glu Val Asp His Ala
        180                 185                 190

Gln Leu Glu Gly Val Glu Ile Ser Thr Arg Ala Lys Lys Lys Leu Glu
    195                 200                 205

Leu Arg Asp Tyr Leu Leu Ser His Pro Glu Ser Ala Ser Leu Ala Ser
210                 215                 220

Leu Leu Glu Ser Tyr Ser Arg Glu Gln Val Asn Phe Phe Val Asp Gln
225                 230                 235                 240

Gly Ala Val Thr Ile Val Gln Lys Glu Val Gln Arg Ser Ala Ala Tyr
            245                 250                 255

Phe Glu Gly Ile Glu Ala Ser Arg Pro Leu Glu Leu Asn Pro Glu Gln
        260                 265                 270

Arg Gln Ala Arg Asp Ala Val Val Ser Ser Ile Gly Ser Ser Gln Pro
    275                 280                 285

Pro Phe Leu Leu Gln Gly Ile Thr Gly Ser Gly Lys Thr Glu Val Tyr
290                 295                 300

Leu Gln Ile Ile Gln Gly Ala Leu Asp Lys Gly Lys Thr Ala Ile Leu
305                 310                 315                 320

Leu Val Pro Glu Ile Ser Leu Thr Pro Gln Met Thr Glu Arg Phe Ile
            325                 330                 335

Ala Arg Phe Gly Asp Lys Val Ala Ile Leu His Ser Gly Leu Ser Asn
        340                 345                 350

Gly Glu Lys Tyr Asp Glu Trp Arg Lys Val Glu Arg Gly Asp Ala Gln
    355                 360                 365

Val Val Val Gly Ala Arg Ser Ala Ile Phe Ala Pro Leu Lys Asn Leu
370                 375                 380

Gly Val Met Ile Ile Asp Glu Glu His Glu Ala Ala Tyr Lys Gln Asp
385                 390                 395                 400

Ser Asn Pro Arg Tyr His Ala Arg Glu Val Ala Ile Leu Arg Ala Gln
            405                 410                 415

Tyr Asn Gln Ala Thr Leu Val Leu Gly Ser Ala Thr Pro Ser Leu Glu
        420                 425                 430

Ser Arg Ala Arg Ala Gly Lys Gly Val Tyr Gln His Leu Arg Leu Thr
    435                 440                 445

Gln Arg Ala Asn Pro Leu Ala Thr Ile Pro Glu Val Gln Val Ile Asp
450                 455                 460

Phe Arg Asp Tyr Ile Gly Gln Asn Glu Thr Ser Asn Phe Thr Pro Pro
465                 470                 475                 480

Leu Leu Glu Ala Ile Gln Asp Arg Leu Val Lys Lys Glu Gln Met Val
            485                 490                 495

Leu Met Leu Asn Arg Arg Gly Tyr Ser Ser Phe Val Met Cys Arg Glu
        500                 505                 510

Cys Gly Thr Val Asp Thr Cys Pro Asn Cys Asp Ile Ser Leu Thr Leu
    515                 520                 525

His Met Asp Thr Lys Thr Met Asn Cys His Tyr Cys Gly Phe Ser Lys
530                 535                 540

Asp Ile Pro Gln Val Cys Pro Asn Cys Lys Ser His Ser Ile Arg Tyr
545                 550                 555                 560

Tyr Gly Thr Gly Thr Gln Lys Ala Tyr Asp Glu Leu Ala Glu Leu Phe
```

```
                        565                 570                 575
Pro Gln Ala Arg Ile Leu Arg Met Asp Val Asp Thr Thr Arg Lys Lys
                580                 585                 590
Gly Ser His Gln Ala Leu Leu Asp Gln Phe Gly Arg Gly Glu Ala Asp
                595                 600                 605
Ile Leu Leu Gly Thr Gln Met Ile Ala Lys Gly Leu Asp Phe Pro Asn
                610                 615                 620
Val Thr Leu Val Gly Val Leu Asn Ala Asp Thr Ala Leu Asn Leu Pro
625                 630                 635                 640
Asp Phe Arg Ser Ser Glu Arg Thr Phe Gln Leu Leu Thr Gln Val Ala
                645                 650                 655
Gly Arg Ala Gly Arg Ala Glu Lys Ala Gly Gln Val Leu Ile Gln Ser
                660                 665                 670
Tyr Asn Pro Gln His Tyr Ala Ile Arg Phe Ala Lys Asp Gln Asp Tyr
                675                 680                 685
Glu Gly Phe Tyr Ala Tyr Glu Met Gly Ile Arg Arg Gln Leu Gly Tyr
                690                 695                 700
Pro Pro Tyr Tyr Phe Thr Ile Gly Ile Thr Leu Ser His Lys Lys Glu
705                 710                 715                 720
Glu Glu Val Phe Lys Arg Ala Tyr Glu Val Met Asn Ile Leu Arg Ser
                725                 730                 735
Gly Leu Ser Glu Thr Ser Pro Ile Leu Gly Pro Thr Pro Lys Pro Ile
                740                 745                 750
Ala Arg Thr His Asn Leu Tyr His Tyr Gln Ile Leu Ile Lys Tyr Arg
                755                 760                 765
Leu Glu Asp Glu Leu Gly Pro Thr Leu Asn Gln Val Leu Ala Leu Thr
                770                 775                 780
Gln Glu Arg Glu Asn Ser Glu Leu Arg Leu Ser Ile Asp His Glu Pro
785                 790                 795                 800
Gln Gln Phe Leu (2) INFORMATION FOR SEQ ID NO:3:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (xi) SEQUENCE DESCRIPTION: SEQ ID NO:3:

GTGAAGCAGT GCGTCGCCGT ATCGAAG                                      27

(2) INFORMATION FOR SEQ ID NO:4:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:4:

ACCATGAGCC GCAGCAATTT TTATAAGAAG                                   30

(2) INFORMATION FOR SEQ ID NO:5:

(i) SEQUENCE CHARACTERISTICS:
        (A) LENGTH: 2415 base pairs
        (B) TYPE: nucleic acid
        (C) STRANDEDNESS: double
```

(D) TOPOLOGY: linear (ix) FEATURE:
  (A) NAME/KEY: Coding Sequence
  (B) LOCATION: 1...2412
  (D) OTHER INFORMATION:

(xi) SEQUENCE DESCRIPTION: SEQ ID NO:5:

| | | | | | | | | | | | | | | | | |
|---|---|---|---|---|---|---|---|---|---|---|---|---|---|---|---|---|
| CAA | GGA | GGA | GGT | GAG | AAG | ATG | GCC | CTA | GCT | AAG | ATT | ATC | GTA | GAT | GTG | 48 |
| Gln | Gly | Gly | Gly | Glu | Lys | Met | Ala | Leu | Ala | Lys | Ile | Ile | Val | Asp | Val | |
| 1 | | | | 5 | | | | 10 | | | | | 15 | | | |
| CCC | TTG | ATG | CAG | ACG | GAC | CAG | CCC | TAT | AGT | TAC | AGG | ATT | CCG | GAG | GAA | 96 |
| Pro | Leu | Met | Gln | Thr | Asp | Gln | Pro | Tyr | Ser | Tyr | Arg | Ile | Pro | Glu | Glu | |
| | | | 20 | | | | | 25 | | | | | 30 | | | |
| TTT | GAG | GGA | ATG | CTG | GAA | GTT | GGG | ATG | CGG | GTT | CAT | GTG | CCT | TTT | GGT | 144 |
| Phe | Glu | Gly | Met | Leu | Glu | Val | Gly | Met | Arg | Val | His | Val | Pro | Phe | Gly | |
| | | 35 | | | | | 40 | | | | | 45 | | | | |
| AAG | GGT | AAT | CGC | CTG | ATT | CAA | GGG | ATT | GTT | CTT | GGT | TTG | GAG | TCC | CAA | 192 |
| Lys | Gly | Asn | Arg | Leu | Ile | Gln | Gly | Ile | Val | Leu | Gly | Leu | Glu | Ser | Gln | |
| 50 | | | | | 55 | | | | | 60 | | | | | | |
| TCA | GAT | GGA | GAA | GAG | ATG | GAG | CAA | GAT | TTA | AAA | GAT | ATT | GCA | GAG | GTG | 240 |
| Ser | Asp | Gly | Glu | Glu | Met | Glu | Gln | Asp | Leu | Lys | Asp | Ile | Ala | Glu | Val | |
| 65 | | | | | 70 | | | | | 75 | | | | | 80 | |
| CTG | GAT | TTT | TCT | CCT | GTT | CTC | ACG | CCA | GAA | CAA | CTC | TGG | CTG | GCT | GAG | 288 |
| Leu | Asp | Phe | Ser | Pro | Val | Leu | Thr | Pro | Glu | Gln | Leu | Trp | Leu | Ala | Glu | |
| | | | | 85 | | | | | 90 | | | | | 95 | | |
| GAG | TTA | CGC | AAA | TCT | GTC | TTC | TCC | TAC | AAA | ATT | TCT | ATC | CTC | AAG | GCC | 336 |
| Glu | Leu | Arg | Lys | Ser | Val | Phe | Ser | Tyr | Lys | Ile | Ser | Ile | Leu | Lys | Ala | |
| | | | 100 | | | | | 105 | | | | | 110 | | | |
| ATG | CTT | CCA | GGA | TTT | CTG | AAT | TCT | AGC | TAT | GAC | AAG | ATT | CTC | TAT | CCT | 384 |
| Met | Leu | Pro | Gly | Phe | Leu | Asn | Ser | Ser | Tyr | Asp | Lys | Ile | Leu | Tyr | Pro | |
| | | | 115 | | | | | 120 | | | | | 125 | | | |
| CTG | GAA | GGC | TTG | AGT | CAG | GAA | GAA | CGA | GTG | CGC | CTG | TTT | GGT | TCA | GAA | 432 |
| Leu | Glu | Gly | Leu | Ser | Gln | Glu | Glu | Arg | Val | Arg | Leu | Phe | Gly | Ser | Glu | |
| | | 130 | | | | | 135 | | | | | 140 | | | | |
| GAT | TCG | CTA | GCC | TTT | TCT | TCA | CTA | GAC | CTT | GCC | AAG | CAA | GCT | GAA | ATG | 480 |
| Asp | Ser | Leu | Ala | Phe | Ser | Ser | Leu | Asp | Leu | Ala | Lys | Gln | Ala | Glu | Met | |
| 145 | | | | | 150 | | | | | 155 | | | | | 160 | |
| ATG | CGT | TTG | ACT | AGA | AAA | GGC | CTG | CTT | GGT | CTG | GAA | TAT | CAG | GCA | GTC | 528 |
| Met | Arg | Leu | Thr | Arg | Lys | Gly | Leu | Leu | Gly | Leu | Glu | Tyr | Gln | Ala | Val | |
| | | | | 165 | | | | | 170 | | | | | 175 | | |
| GAT | CAA | AAG | AAG | GTC | AAG | ACC | CAG | TCT | TGG | TAT | GAG | GTT | GAC | CAT | GCT | 576 |
| Asp | Gln | Lys | Lys | Val | Lys | Thr | Gln | Ser | Trp | Tyr | Glu | Val | Asp | His | Ala | |
| | | | 180 | | | | | 185 | | | | | 190 | | | |
| CAA | TTA | GAA | GGT | GTT | GAG | ATT | TCT | ACA | CGT | GCC | AAG | AAA | AAG | TTG | GAA | 624 |
| Gln | Leu | Glu | Gly | Val | Glu | Ile | Ser | Thr | Arg | Ala | Lys | Lys | Lys | Leu | Glu | |
| | | | | 195 | | | | | 200 | | | | | 205 | | |
| CTG | AGA | GAT | TAT | CTG | CTG | TCT | CAT | CCA | GAG | AGC | GCT | TCC | TTG | GCT | AGC | 672 |
| Leu | Arg | Asp | Tyr | Leu | Leu | Ser | His | Pro | Glu | Ser | Ala | Ser | Leu | Ala | Ser | |
| | 210 | | | | | 215 | | | | | 220 | | | | | |
| TTG | TTA | GAG | TCC | TAC | TCG | CGA | GAG | CAA | GTC | AAC | TTC | TTT | GTG | GAT | CAA | 720 |
| Leu | Leu | Glu | Ser | Tyr | Ser | Arg | Glu | Gln | Val | Asn | Phe | Phe | Val | Asp | Gln | |
| 225 | | | | | 230 | | | | | 235 | | | | | 240 | |
| GGT | GCT | GTT | ACC | ATA | GTC | CAA | AAG | GAA | GTT | CAA | CGC | TCG | GCT | GCT | TAT | 768 |
| Gly | Ala | Val | Thr | Ile | Val | Gln | Lys | Glu | Val | Gln | Arg | Ser | Ala | Ala | Tyr | |
| | | | | 245 | | | | | 250 | | | | | 255 | | |
| TTT | GAA | GGA | ATT | GAA | GCA | AGT | AGA | CCT | TTG | GAG | TTA | AAT | CCA | GAA | CAA | 816 |
| Phe | Glu | Gly | Ile | Glu | Ala | Ser | Arg | Pro | Leu | Glu | Leu | Asn | Pro | Glu | Gln | |
| | | | 260 | | | | | 265 | | | | | 270 | | | |
| AGA | CAG | GCG | CGT | GAT | GCG | GTT | GTG | AGT | TCT | ATT | GGC | AGT | TCT | CAA | CCT | 864 |
| Arg | Gln | Ala | Arg | Asp | Ala | Val | Val | Ser | Ser | Ile | Gly | Ser | Ser | Gln | Pro | |

-continued

|  |  |  |  |  |  |  |  |  |  |  |  |  |  |  |  |
|---|---|---|---|---|---|---|---|---|---|---|---|---|---|---|---|
|  |  |  | 275 |  |  |  | 280 |  |  |  | 285 |  |  |  |  |
| CCC | TTT | CTA | CTT | CAA | GGG | ATT | ACA | GGA | AGT | GGG | AAG | ACC | GAG | GTT | TAC | 912 |
| Pro | Phe | Leu | Leu | Gln | Gly | Ile | Thr | Gly | Ser | Gly | Lys | Thr | Glu | Val | Tyr |  |
|  |  | 290 |  |  |  |  | 295 |  |  |  |  | 300 |  |  |  |  |
| TTG | CAG | ATT | ATC | CAA | GGT | GCC | CTG | GAT | AAG | GGC | AAG | ACA | GCT | ATT | TTG | 960 |
| Leu | Gln | Ile | Ile | Gln | Gly | Ala | Leu | Asp | Lys | Gly | Lys | Thr | Ala | Ile | Leu |  |
| 305 |  |  |  |  | 310 |  |  |  |  | 315 |  |  |  |  | 320 |  |
| CTG | GTA | CCT | GAG | ATT | TCC | TTG | ACT | CCT | CAG | ATG | ACC | GAG | CGT | TTT | ATA | 1008 |
| Leu | Val | Pro | Glu | Ile | Ser | Leu | Thr | Pro | Gln | Met | Thr | Glu | Arg | Phe | Ile |  |
|  |  |  |  | 325 |  |  |  |  | 330 |  |  |  |  | 335 |  |  |
| GCA | CGT | TTT | GGG | GAC | AAG | GTA | GCC | ATT | CTT | CAC | TCA | GGA | TTA | TCC | AAT | 1056 |
| Ala | Arg | Phe | Gly | Asp | Lys | Val | Ala | Ile | Leu | His | Ser | Gly | Leu | Ser | Asn |  |
|  |  |  | 340 |  |  |  |  | 345 |  |  |  |  | 350 |  |  |  |
| GGT | GAA | AAG | TAT | GAT | GAA | TGG | CGC | AAG | GTG | GAG | CGT | GGC | GAT | GCC | CAA | 1104 |
| Gly | Glu | Lys | Tyr | Asp | Glu | Trp | Arg | Lys | Val | Glu | Arg | Gly | Asp | Ala | Gln |  |
|  |  | 355 |  |  |  |  | 360 |  |  |  |  | 365 |  |  |  |  |
| GTT | GTT | GTT | GGT | GCC | AGA | TCT | GCT | ATC | TTT | GCT | CCT | CTG | AAA | AAT | CTG | 1152 |
| Val | Val | Val | Gly | Ala | Arg | Ser | Ala | Ile | Phe | Ala | Pro | Leu | Lys | Asn | Leu |  |
|  |  | 370 |  |  |  |  | 375 |  |  |  |  | 380 |  |  |  |  |
| GGT | GTC | ATG | ATT | ATT | GAT | GAA | GAG | CAT | GAA | GCG | GCT | TAT | AAG | CAG | GAC | 1200 |
| Gly | Val | Met | Ile | Ile | Asp | Glu | Glu | His | Glu | Ala | Ala | Tyr | Lys | Gln | Asp |  |
| 385 |  |  |  |  | 390 |  |  |  |  | 395 |  |  |  |  | 400 |  |
| AGC | AAT | CCC | CGT | TAC | CAT | GCC | AGA | GAG | GTA | GCT | ATT | TTA | CGG | GCT | CAG | 1248 |
| Ser | Asn | Pro | Arg | Tyr | His | Ala | Arg | Glu | Val | Ala | Ile | Leu | Arg | Ala | Gln |  |
|  |  |  |  | 405 |  |  |  |  | 410 |  |  |  |  | 415 |  |  |
| TAT | AAT | CAA | GCA | ACT | CTG | GTA | CTT | GGA | TCT | GCA | ACG | CCG | AGC | TTA | GAG | 1296 |
| Tyr | Asn | Gln | Ala | Thr | Leu | Val | Leu | Gly | Ser | Ala | Thr | Pro | Ser | Leu | Glu |  |
|  |  |  | 420 |  |  |  |  | 425 |  |  |  |  | 430 |  |  |  |
| AGC | CGG | GCA | CGT | GCT | GGC | AAA | GGC | GTC | TAT | CAA | CAC | TTA | CGT | CTA | ACC | 1344 |
| Ser | Arg | Ala | Arg | Ala | Gly | Lys | Gly | Val | Tyr | Gln | His | Leu | Arg | Leu | Thr |  |
|  |  | 435 |  |  |  |  | 440 |  |  |  |  | 445 |  |  |  |  |
| CAA | CGT | GCC | AAT | CCT | TTG | GCT | ACA | ATC | CCT | GAG | GTT | CAA | GTG | ATT | GAC | 1392 |
| Gln | Arg | Ala | Asn | Pro | Leu | Ala | Thr | Ile | Pro | Glu | Val | Gln | Val | Ile | Asp |  |
|  | 450 |  |  |  |  | 455 |  |  |  |  | 460 |  |  |  |  |  |
| TTT | CGA | GAC | TAT | ATC | GGA | CAA | AAT | GAG | ACG | TCA | AAC | TTT | ACG | CCT | CCT | 1440 |
| Phe | Arg | Asp | Tyr | Ile | Gly | Gln | Asn | Glu | Thr | Ser | Asn | Phe | Thr | Pro | Pro |  |
| 465 |  |  |  |  | 470 |  |  |  |  | 475 |  |  |  |  | 480 |  |
| TTG | CTA | GAG | GCT | ATC | CAA | GAC | CGT | CTG | GTT | AAA | AAA | GAG | CAG | ATG | GTT | 1488 |
| Leu | Leu | Glu | Ala | Ile | Gln | Asp | Arg | Leu | Val | Lys | Lys | Glu | Gln | Met | Val |  |
|  |  |  |  | 485 |  |  |  |  | 490 |  |  |  |  | 495 |  |  |
| CTC | ATG | CTC | AAT | CGC | CGT | GGT | TAT | TCT | AGC | TTT | GTC | ATG | TGT | CGG | GAG | 1536 |
| Leu | Met | Leu | Asn | Arg | Arg | Gly | Tyr | Ser | Ser | Phe | Val | Met | Cys | Arg | Glu |  |
|  |  |  | 500 |  |  |  |  | 505 |  |  |  |  | 510 |  |  |  |
| TGT | GGG | ACG | GTG | GAT | ACT | TGT | CCC | AAC | TGT | GAT | ATT | TCT | CTG | ACC | TTG | 1584 |
| Cys | Gly | Thr | Val | Asp | Thr | Cys | Pro | Asn | Cys | Asp | Ile | Ser | Leu | Thr | Leu |  |
|  |  | 515 |  |  |  |  | 520 |  |  |  |  | 525 |  |  |  |  |
| CAT | ATG | GAT | ACC | AAG | ACT | ATG | AAC | TGC | CAT | TAT | TGT | GGT | TTC | TCG | AAG | 1632 |
| His | Met | Asp | Thr | Lys | Thr | Met | Asn | Cys | His | Tyr | Cys | Gly | Phe | Ser | Lys |  |
|  | 530 |  |  |  |  | 535 |  |  |  |  | 540 |  |  |  |  |  |
| GAT | ATT | CCT | CAG | GTC | TGT | CCT | AAC | TGT | AAG | AGC | CAC | AGT | ATT | CGT | TAC | 1680 |
| Asp | Ile | Pro | Gln | Val | Cys | Pro | Asn | Cys | Lys | Ser | His | Ser | Ile | Arg | Tyr |  |
| 545 |  |  |  |  | 550 |  |  |  |  | 555 |  |  |  |  | 560 |  |
| TAT | GGG | ACG | GGA | ACT | CAG | AAG | GCT | TAT | GAT | GAG | CTA | GCA | GAA | CTC | TTT | 1728 |
| Tyr | Gly | Thr | Gly | Thr | Gln | Lys | Ala | Tyr | Asp | Glu | Leu | Ala | Glu | Leu | Phe |  |
|  |  |  |  | 565 |  |  |  |  | 570 |  |  |  |  | 575 |  |  |
| CCC | CAA | GCT | CGC | ATT | TTG | AGG | ATG | GAT | GTG | GAT | ACG | ACT | CGA | AAG | AAA | 1776 |
| Pro | Gln | Ala | Arg | Ile | Leu | Arg | Met | Asp | Val | Asp | Thr | Thr | Arg | Lys | Lys |  |
|  |  |  | 580 |  |  |  |  | 585 |  |  |  |  | 590 |  |  |  |
| GGC | AGT | CAC | CAA | GCC | TTG | CTT | GAC | CAG | TTT | GGG | CGA | GGG | GAA | GCG | GAT | 1824 |

-continued

```
Gly Ser His Gln Ala Leu Leu Asp Gln Phe Gly Arg Gly Glu Ala Asp
        595                 600                 605
ATT TTA CTT GGT ACT CAG ATG ATT GCA AAG GGT TTG GAT TTT CCC AAT      1872
Ile Leu Leu Gly Thr Gln Met Ile Ala Lys Gly Leu Asp Phe Pro Asn
        610                 615                 620
GTT ACC CTA GTC GGA GTT CTA AAT GCG GAT ACG GCC TTG AAT CTG CCT      1920
Val Thr Leu Val Gly Val Leu Asn Ala Asp Thr Ala Leu Asn Leu Pro
625                 630                 635                 640
GAT TTC CGT TCT TCT GAG AGA ACC TTC CAG CTC TTG ACT CAG GTG GCA      1968
Asp Phe Arg Ser Ser Glu Arg Thr Phe Gln Leu Leu Thr Gln Val Ala
                645                 650                 655
GGT CGA GCA GGT CGT GCT GAA AAG GCA GGT CAA GTC TTG ATA CAG TCC      2016
Gly Arg Ala Gly Arg Ala Glu Lys Ala Gly Gln Val Leu Ile Gln Ser
        660                 665                 670
TAC AAT CCG CAG CAC TAT GCT ATT CGA TTT GCC AAG GAT CAA GAT TAC      2064
Tyr Asn Pro Gln His Tyr Ala Ile Arg Phe Ala Lys Asp Gln Asp Tyr
        675                 680                 685
GAA GGC TTT TAT GCC TAT GAA ATG GGA ATC AGA CGA CAA CTC GGC TAT      2112
Glu Gly Phe Tyr Ala Tyr Glu Met Gly Ile Arg Arg Gln Leu Gly Tyr
        690                 695                 700
CCA CCT TAC TAT TTC ACG ATT GGT ATT ACC CTT TCT CAC AAG AAA GAA      2160
Pro Pro Tyr Tyr Phe Thr Ile Gly Ile Thr Leu Ser His Lys Lys Glu
705                 710                 715                 720
GAA GAG GTT TTC AAA CGT GCC TAT GAA GTC ATG AAC ATT TTG CGG TCA      2208
Glu Glu Val Phe Lys Arg Ala Tyr Glu Val Met Asn Ile Leu Arg Ser
                725                 730                 735
GGC TTG TCA GAG ACC AGT CCC ATT CTG GGG CCA ACG CCA AAA CCG ATT      2256
Gly Leu Ser Glu Thr Ser Pro Ile Leu Gly Pro Thr Pro Lys Pro Ile
                740                 745                 750
GCC CGT ACC CAC AAC CTC TAT CAT TAC CAG ATT TTA ATT AAA TAC CGT      2304
Ala Arg Thr His Asn Leu Tyr His Tyr Gln Ile Leu Ile Lys Tyr Arg
        755                 760                 765
TTA GAA GAT GAG CTG GGG CCG ACC CTC AAC CAG GTC CTG GCC TTG ACT      2352
Leu Glu Asp Glu Leu Gly Pro Thr Leu Asn Gln Val Leu Ala Leu Thr
        770                 775                 780
CAA GAA CGG GAA AAT AGT GAG CTC CGT CTC AGC ATT GAC CAT GAG CCG      2400
Gln Glu Arg Glu Asn Ser Glu Leu Arg Leu Ser Ile Asp His Glu Pro
785                 790                 795                 800
CAG CAA TTT TTA TAA                                                  2415
Gln Gln Phe Leu
```